(12) United States Patent
He et al.

(10) Patent No.: US 10,742,269 B2
(45) Date of Patent: Aug. 11, 2020

(54) SYSTEMS, DEVICES, AND METHODS UTILIZING SECONDARY COMMUNICATION SYSTEMS

(71) Applicant: ABBOTT DIABETES CARE INC., Alameda, CA (US)

(72) Inventors: Lei He, Moraga, CA (US); Daniel M. Bernstein, El Granada, CA (US); Michael R. Love, Pleasanton, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 0 days.

(21) Appl. No.: 16/556,734

(22) Filed: Aug. 30, 2019

(65) Prior Publication Data

US 2019/0386711 A1 Dec. 19, 2019

Related U.S. Application Data

(63) Continuation of application No. PCT/US2018/020012, filed on Feb. 27, 2018.

(60) Provisional application No. 62/466,292, filed on Mar. 2, 2017.

(51) Int. Cl.
| | |
|---|---|
| *H04B 5/00* | (2006.01) |
| *A61B 5/145* | (2006.01) |
| *A61B 5/00* | (2006.01) |
| *H01Q 1/27* | (2006.01) |
| *H01Q 7/00* | (2006.01) |

(52) U.S. Cl.
CPC ....... *H04B 5/0093* (2013.01); *A61B 5/14532* (2013.01); *A61B 5/6833* (2013.01); *H01Q 1/273* (2013.01); *H01Q 7/00* (2013.01)

(58) Field of Classification Search
CPC .......... G16H 40/67; H01Q 1/273; H01Q 7/00; H04B 5/0093; A61B 5/14532; A61B 5/6833; A61B 5/6801; A61B 5/6846; A61B 5/6813; A61B 5/683; A61B 5/6832; A61B 5/6847; A61B 5/6867
See application file for complete search history.

(56) References Cited

U.S. PATENT DOCUMENTS

| | | | |
|---|---|---|---|
| 6,169,925 B1* | 1/2001 | Villaseca | A61N 1/37229 128/903 |
| 8,570,187 B2* | 10/2013 | Janna | H01Q 7/02 340/870.31 |
| 8,938,305 B2 | 1/2015 | Abrahamson et al. | |

(Continued)

OTHER PUBLICATIONS

WO, PCT/US2018/020012 ISR and Written Opinion, dated Jun. 14, 2018.

(Continued)

*Primary Examiner* — Devan A Sandiford
(74) *Attorney, Agent, or Firm* — One LLP

(57) ABSTRACT

Embodiments of devices that improve radio frequency (RF) communication between an on body device and a second device are disclosed. Some of these embodiments pertain to a secondary communication system that captures an RF signal transmitted in a first directional pattern and retransmits it in the second directional pattern. Other embodiments pertain to a secondary communication system that provides an additional antenna positioned in a different location with which a user can communicate.

20 Claims, 18 Drawing Sheets

(56) References Cited

U.S. PATENT DOCUMENTS

| | | | | |
|---|---|---|---|---|
| 2005/0283207 | A1* | 12/2005 | Hochmair | A61N 1/37217 607/55 |
| 2007/0038051 | A1* | 2/2007 | Talman | A61B 3/16 600/345 |
| 2008/0009692 | A1* | 1/2008 | Stafford | A61B 5/6833 600/345 |
| 2008/0288024 | A1* | 11/2008 | Abrahamson | A61N 1/37223 607/60 |
| 2010/0094111 | A1* | 4/2010 | Heller | A61B 5/14532 600/345 |
| 2011/0193704 | A1* | 8/2011 | Harper | A61B 5/7275 340/573.1 |
| 2011/0213225 | A1* | 9/2011 | Bernstein | G06Q 50/22 600/309 |
| 2011/0319729 | A1* | 12/2011 | Donnay | A61B 5/15087 600/309 |
| 2012/0026009 | A1* | 2/2012 | Zhao | A61N 1/37229 340/870.28 |
| 2012/0100887 | A1* | 4/2012 | Tekin | A61B 5/0022 455/556.1 |
| 2012/0157824 | A1* | 6/2012 | Bossmann | C12Q 1/37 600/420 |
| 2012/0313830 | A1* | 12/2012 | Lee | H01Q 5/392 343/729 |
| 2013/0085537 | A1* | 4/2013 | Mashiach | A61N 2/02 607/3 |
| 2014/0039579 | A1* | 2/2014 | Mashiach | A61N 1/0551 607/61 |
| 2015/0005606 | A1* | 1/2015 | Honore | A61B 5/14532 600/365 |
| 2015/0018639 | A1* | 1/2015 | Stafford | A61B 5/0002 600/309 |
| 2015/0025345 | A1* | 1/2015 | Funderburk | A61B 5/1451 600/345 |
| 2015/0173661 | A1* | 6/2015 | Myles | A61B 5/14503 600/365 |
| 2016/0361550 | A1* | 12/2016 | Landherr | H01Q 1/273 |
| 2017/0074757 | A1* | 3/2017 | Garcia | A61B 5/743 |
| 2019/0320947 | A1* | 10/2019 | Chen | A61B 5/14546 |

OTHER PUBLICATIONS

Specification of the Bluetooth System, vol. 0—Master Table of Contents & Compliance Requirements, Covered Core Package version: 4.0, Jun. 30, 2010.

Specification of the Bluetooth System, vol. 1—Architecture & Terminology Overview, Covered Core Package version: 4.0, Jun. 30, 2010.

Specification of the Bluetooth System, vol. 2—Core System Package [BR/EDR Controller volume], Covered Core Package version: 4.0, Jun. 30, 2010.

Specification of the Bluetooth System, vol. 3—Core System Package [Host volume], Covered Core Package version: 4.0, Jun. 30, 2010.

Specification of the Bluetooth System, vol. 4—Host Controller Interface [Transport Layer], Covered Core Package version: 4.0, Jun. 30, 2010.

Specification of the Bluetooth System, vol. 5—Core System Package [AMP Controller volume], Covered Core Package version: 4.0, Jun. 30, 2010.

Specification of the Bluetooth System, vol. 6—Core System Package [Low Energy Controller volume], Covered Core Package version: 4.0, Jun. 30, 2010.

Specification of the Bluetooth System, vol. 0—Master Table of Contents & Compliance Requirements, Covered Core Package version: 4.2, Dec. 2, 2014.

Specification of the Bluetooth System, vol. 1—Architecture & Terminology Overview, Covered Core Package version: 4.2, Dec. 2, 2014.

Specification of the Bluetooth System, vol. 2—Core System Package [BR/EDR Controller volume], Covered Core Package version: 4.2, Dec. 2, 2014.

Specification of the Bluetooth System, vol. 3—Core System Package [Host volume], Covered Core Package version: 4.2, Dec. 2, 2014.

Specification of the Bluetooth System, vol. 4—Host Controller Interface [Transport Layer], Covered Core Package version: 4.2, Dec. 2, 2014.

Specification of the Bluetooth System, vol. 5—Core System Package [AMP Controller volume], Covered Core Package version: 4.2, Dec. 2, 2014.

Specification of the Bluetooth System, vol. 6—Core System Package [Low Energy Controller volume], Covered Core Package version: 4.2, Dec. 2, 2014.

Specification of the Bluetooth System, vol. 7—Core System Package [Wireless Coexistence volume], Covered Core Package version: 4.2, Dec. 2, 2014.

* cited by examiner

SYSTEMS, DEVICES, AND METHODS UTILIZING SECONDARY COMMUNICATION SYSTEMS

CROSS-REFERENCE TO RELATED APPLICATIONS

The present application is a continuation of International Patent Application No. PCT/US2018/020012, filed Feb. 27, 2018, which claims priority to and the benefit of U.S. Provisional Patent Application No. 62/466,292, filed Mar. 2, 2017, both of which are incorporated by reference herein in their entireties for all purposes.

FIELD

The subject matter described herein relates generally to systems, devices, and methods for radio frequency (RF) communications between electrical devices, and more particularly to the improvement of RF communications between an on body device and a second device.

BACKGROUND

A number of systems have been developed for measuring data with a device located on or near the body of a user. These on body devices typically include one or more sensors and communication circuitry for wirelessly transmitting the data or other information from the on body device to a second electrical device.

A common application for on body devices is the automatic monitoring of analytes, like glucose, in bodily fluid such as in blood, in interstitial fluid (ISF), dermal fluid of the dermal layer, or in other biological fluid of the wearer. Such analyte monitoring devices have particular value in the management of diabetes.

These systems can provide a determination of analyte levels, or readings, over time to a health care provider (HCP), a diabetic patient, and/or a caregiver. Knowing the current analyte level and how it may change over time can be useful in determining the appropriate treatment for managing the diabetes condition.

In some cases, the on body device is positioned on the body of the wearer in a location chosen to facilitate the collection of data, but that may not be convenient for the subsequent wireless transmission of that data to a second device. In other cases, the on body device may be positioned in a location that facilitates wireless transmission but the on body device itself may transmit in a directional pattern that is not optimal for short range communications, such as those using Bluetooth or Bluetooth Low Energy. In certain other instances, the receiving second device may be positioned in a location that is partially shielded from the on body device making communication difficult without a relative boost to the transmission signal in the proper direction.

For these and other reasons, there exists a need for improved RF communication between an on body device and a second device.

SUMMARY

Example embodiments of systems, devices, and methods are described herein for improving RF communication between an on body device and a second device. The embodiments that are described are examples only and not intended to serve as an exhaustive description of all manners in which the disclosed concepts can be implemented, as those of ordinary skill in the art will readily recognize upon reading the present disclosure.

A number of example embodiments are described that permit an on body device having one or more main antennas to utilize a secondary communication system that captures the RF signal transmitted by the one or more main antennas and re-transmits it in a different directional pattern. For example, an on body device having a main antenna with a generally unidirectional transmission pattern can utilize the secondary communication system, e.g., in the form of an RF redirection device, to capture and retransmit the main antennas signal in a multidirectional, or omnidirectional, transmission pattern. Example embodiments of the RF redirection device can include one or more primary antennas coupled with one or more secondary antennas, where the one or more primary antennas are adapted to receive the signal from the main antenna and provided to the one or more secondary antennas that are, in turn, adapted to transmit in a different directional pattern than the main antenna. A number of example implementations of this secondary communication system are disclosed.

Also, a number of example embodiments are described that permit an on body device having one or more main antennas to utilize a secondary communication system that provides a secondary antenna in a location spaced apart from the one or more main antennas. For example, an on body device having a main antenna can transmit via a first magnetic coupling to a primary antenna that is electrically connected to a secondary antenna. The secondary antenna can transmit via a second magnetic coupling to a receiving second device and vice versa.

Other systems, devices, methods, features and advantages of the subject matter described herein will be or will become apparent to one with skill in the art upon examination of the following figures and detailed description. It is intended that all such additional systems, methods, features and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF FIGURES

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

DETAILED DESCRIPTION

Figure 1A:
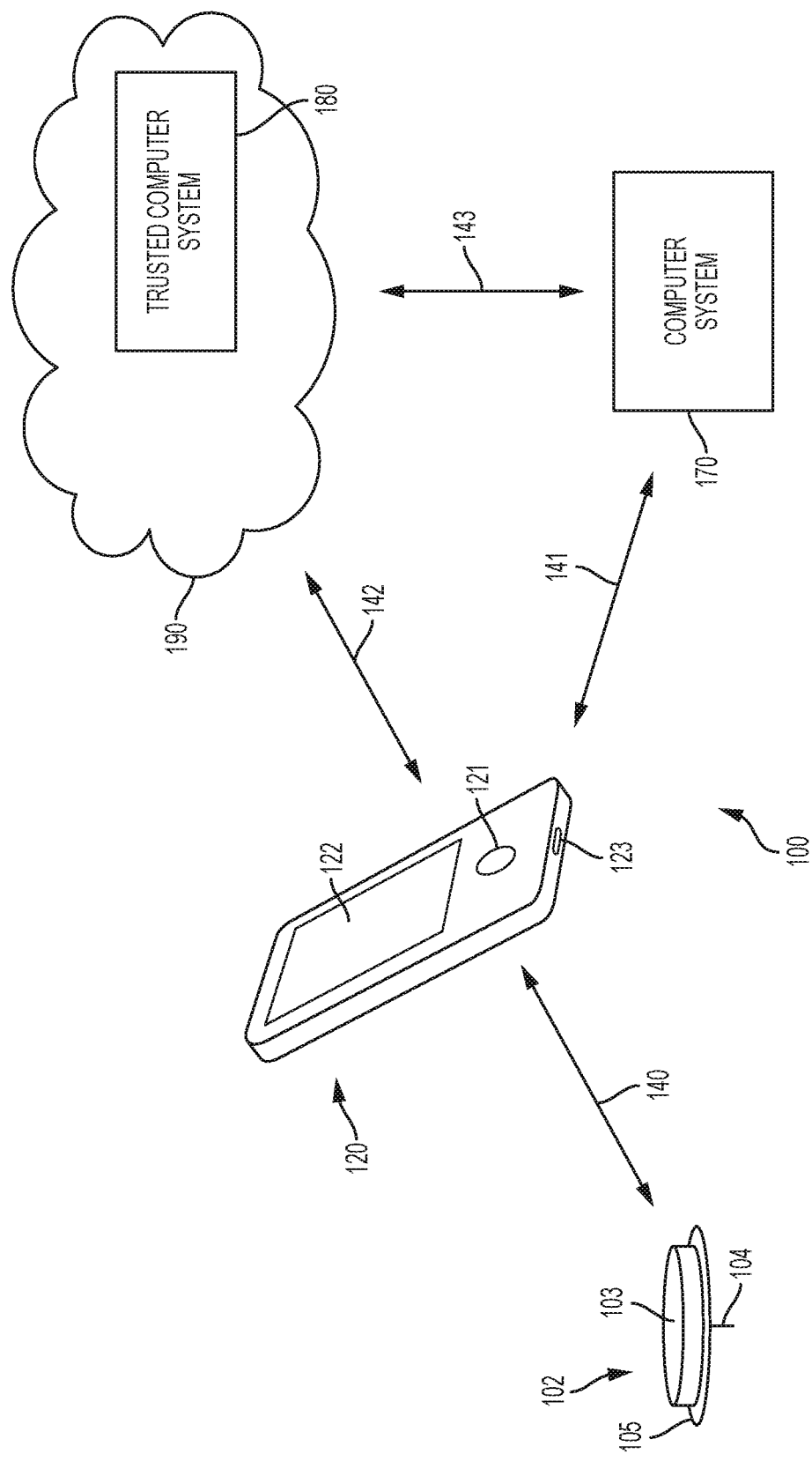
FIG. 1A is an illustrative view depicting an example embodiment of an in vivo analyte monitoring system.

Before the present subject matter is described in detail, it is to be understood that this disclosure is not limited to the particular embodiments described, as such may, of course, vary. It is also to be understood that the terminology used herein is for the purpose of describing particular embodiments only, and is not intended to be limiting, since the scope of the present disclosure will be limited only by the appended claims.

Generally, embodiments of the present disclosure are used with systems, devices, and methods for detecting at least one analyte, such as glucose, in a bodily fluid (e.g., subcutaneously within the interstitial fluid ("ISF") or blood, within the dermal fluid of the dermal layer, or otherwise). Accordingly, many embodiments include in vivo analyte sensors structurally configured so that at least a portion of the sensor is, or can be, positioned in the body of a user to obtain information about at least one analyte of the body. However, the embodiments disclosed herein can be used with in vivo analyte monitoring systems that incorporate in vitro capability, as well as purely in vitro or ex vivo analyte monitoring systems, including those systems that are entirely non-invasive.

Furthermore, the embodiments described herein can be used with devices that sense biometrics other than analyte data, such as heart rate, blood pressure, body temperature, perspiration, intraocular pressure, and others. The embodiments described herein can be used with devices that sense movement and/or activity level alone or in combination with any other metric. The embodiments described herein are thus not limited to medical applications and can be used with other, non-medical systems, where RF communication between devices is employed.

Before describing the embodiments in detail, however, it is first desirable to describe examples of devices that can be present within, for example, an in vivo analyte monitoring system, as well as examples of their operation, all of which can be used with the embodiments described herein.

Example Embodiments of Analyte Monitoring Systems

There are various types of analyte monitoring systems. "Continuous Analyte Monitoring" systems (or "Continuous Glucose Monitoring" systems), for example, are in vivo systems that can transmit data from a sensor control device to a reader device repeatedly or continuously without prompting, e.g., automatically according to a schedule. "Flash Analyte Monitoring" systems (or "Flash Glucose Monitoring" systems or simply "Flash" systems), as another example, are in vivo systems that can transfer data from a sensor control device in response to a scan or request for data by a reader device, such as with a Near Field Communication (NFC) or Radio Frequency Identification (RFID) protocol. In vivo analyte monitoring systems can also operate without the need for finger stick calibration.

In vivo monitoring systems can include a sensor that, while positioned in vivo, makes contact with the bodily fluid of the user and senses the analyte levels contained therein. The sensor can be part of a sensor control device that resides on the body of the user and contains the electronics and power supply that enable and control the analyte sensing. The sensor control device, and variations thereof, can also be referred to as a "sensor control unit," an "on-body electronics" device or unit, an "on-body" device or unit, or a "sensor data communication" device or unit, to name a few. As used herein, these terms are not limited to devices with analyte sensors, and encompass devices that have sensors of other types, whether biometric or non-biometric.

The term "on body" refers to any device that resides directly on the body or in close proximity to the body, such as a wearable device (e.g., glasses, wristband or bracelet, neckband or necklace, etc.).

In vivo monitoring systems can also include one or more reader devices that receive sensed analyte data from the sensor control device. These reader devices can process and/or display the sensed analyte data, in any number of forms, to the user. These devices, and variations thereof, can be referred to as "handheld reader devices," "reader devices" (or simply, "readers"), "handheld electronics" (or handhelds), "portable data processing" devices or units, "data receivers," "receiver" devices or units (or simply receivers), "relay" devices or units, or "remote" devices or units, to name a few. Other devices such as personal computers have also been utilized with or incorporated into in vivo and in vitro monitoring systems.

In vivo analyte monitoring systems can be differentiated from "in vitro" systems that contact a biological sample outside of the body (or rather "ex vivo") and that typically include a meter device that has a port for receiving an analyte test strip carrying a bodily fluid of the user, which can be analyzed to determine the user's analyte level. As mentioned, the embodiments described herein can be used with in vivo systems, in vitro systems, and combinations thereof.

The embodiments described herein can be used to monitor and/or process information regarding any number of one or more different analytes. Analytes that may be monitored include, but are not limited to, acetyl choline, amylase, bilirubin, cholesterol, chorionic gonadotropin, glycosylated hemoglobin (HbA1c), creatine kinase (e.g., CK-MB), creatine, creatinine, DNA, fructosamine, glucose, glucose derivatives, glutamine, growth hormones, hormones, ketones, ketone bodies, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In embodiments that monitor more than one analyte, the analytes may be monitored at the same or different times FIG. 1A is an illustrative view depicting an example embodiment of an in vivo analyte monitoring system 100 having a sensor control device 102 and a reader device 120 that communicate with each other over a local communication path (or link) 140, which can be wired or wireless, and uni-directional or bi-directional. In embodiments where path 140 is wireless, a near field communication (NFC) protocol, RFID protocol, Bluetooth or Bluetooth Low Energy protocol, Wi-Fi protocol, proprietary protocol, or the like can be used, including those communication protocols in existence as of the date of this filing or their later developed variants.

Bluetooth is a well-known standardized short range wireless communication protocol, and Bluetooth Low Energy is a version of the same that requires relatively less power to operate. Bluetooth Low Energy (Bluetooth LE, BTLE, BLE) is also referred to as Bluetooth Smart or Bluetooth Smart Ready. Some examples of Bluetooth and BTLE devices operate in the range of 2.4 to 2.5 Gigahertz (Ghz). BTLE is described in the Bluetooth Specification, version 4.0, published Jun. 30, 2010, and version 4.2, published Dec. 2, 2014, which are incorporated by reference herein in their entirety and for all purposes.

The terms "Near Field Communication" and its acronym "NFC" refer to a number of protocols (or standards) that set forth operating parameters, modulation schemes, coding, transfer speeds, frame format, and command definitions for NFC devices. Some examples of NFC devices operate at 13.56 Megahertz (Mhz). The following is a non-exhaustive list of examples of these protocols: ECMA-340, ECMA-352, ISO/IEC 14443, ISO/IEC 15693, ISO/IEC 18000-3, ISO/IEC 18092, and ISO/IEC 21481, all of which are incorporated by reference herein in their entirety and for all purposes.

Reader device 120 is also capable of wired, wireless, or combined communication with a computer system 170 (e.g., a local or remote computer system) over communication path (or link) 141 and with a network 190, such as the internet or the cloud, over communication path (or link) 142. Communication with network 190 can involve communication with trusted computer system 180 within network 190, or though network 190 to computer system 170 via communication link (or path) 143. Communication paths 141, 142, and 143 can be wireless, wired, or both, can be uni-directional or bi-directional, and can be part of a telecommunications network, such as a Wi-Fi network, a local area network (LAN), a wide area network (WAN), the internet, or other data network. In some cases, communication paths 141 and 142 can be the same path. All communications over paths 140, 141, and 142 can be encrypted and sensor control device 102, reader device 120, computer system 170, and trusted computer system 180 can each be configured to encrypt and decrypt those communications sent and received.

Variants of devices 102 and 120, as well as other components of an in vivo-based analyte monitoring system that are suitable for use with the system, device, and method embodiments set forth herein, are described in U.S. Patent Publication No. 2011/0213225 (the '225 Publication), which is incorporated by reference herein in its entirety for all purposes.

Sensor control device 102 can include a housing 103 containing in vivo analyte monitoring circuitry and a power source. In this embodiment, the in vivo analyte monitoring circuitry is electrically coupled with an analyte sensor 104 that extends through an adhesive patch 105 and projects away from housing 103. Adhesive patch 105 contains an adhesive layer (not shown) for attachment to a skin surface of the body of the user. Other forms of body attachment to the body may be used, in addition to or instead of adhesive.

Sensor 104 is adapted to be at least partially inserted into the body of the user, where it can make fluid contact with that user's bodily fluid (e.g., ISF, dermal fluid, or blood) and be used, along with the in vivo analyte monitoring circuitry, to measure analyte-related data of the user. Sensor 104 and any accompanying sensor control electronics can be applied to the body in any desired manner. For example, an insertion device (not shown) can be used to position all or a portion of analyte sensor 104 through an external surface of the user's skin and into contact with the user's bodily fluid. In doing so, the insertion device can also position sensor control device 102 with adhesive patch 105 onto the skin. In other embodiments, insertion device can position sensor 104 first, and then accompanying sensor control electronics can be coupled with sensor 104 afterwards, either manually or with the aid of a mechanical device. Examples of insertion devices are described in U.S. Patent Publication Nos. 2008/0009692, 2011/0319729, 2015/0018639, 2015/0025345, and 2015/0173661, all which are incorporated by reference herein in their entireties and for all purposes.

After collecting raw data from the user's body, sensor control device 102 can apply analog signal conditioning to the data and convert the data into a digital form of the conditioned raw data. In some embodiments, this conditioned raw digital data can be encoded for transmission to another device, e.g., reader device 120, which then algorithmically processes that digital raw data into a final form representative of the user's measured biometric (e.g., a form readily made suitable for display to the user). This algorithmically processed data can then be formatted or graphically processed for digital display to the user. In other embodiments, sensor control device 102 can algorithmically process the digital raw data into the final form that is representative of the user's measured biometric (e.g., analyte level) and then encode and wirelessly communicate that data to reader device 120, which in turn can format or graphically process the received data for digital display to the user. In other embodiments, sensor control device 102 can graphically process the final form of the data such that it is ready for display, and display that data on a display of sensor control device 102 or transmit the data to reader device 120. In some embodiments, the final form of the biometric data (prior to graphic processing) is used by the system (e.g., incorporated into a diabetes monitoring regime) without processing for display to the user. In some embodiments, sensor control device 102 and reader device 120 transmit the digital raw data to another computer system for algorithmic processing and display.

Reader device 120 can include a display 122 to output information to the user and/or to accept an input from the user, and an optional input component 121 (or more), such as a button, actuator, touch sensitive switch, capacitive switch, pressure sensitive switch, jog wheel or the like, to input data, commands, or otherwise control the operation of reader device 120. In certain embodiments, display 122 and input component 121 may be integrated into a single component, for example, where the display can detect the presence and location of a physical contact touch upon the display, such as a touch screen user interface. In certain embodiments, input component 121 of reader device 120 may include a microphone and reader device 120 may include software configured to analyze audio input received from the microphone, such that functions and operation of the reader device 120 may be controlled by voice commands. In certain embodiments, an output component of reader device 120 includes a speaker (not shown) for outputting information as audible signals. Similar voice responsive components such as a speaker, microphone and software routines to generate, process and store voice driven signals may be included in sensor control device 102.

Reader device 120 can also include one or more data communication ports 123 for wired data communication with external devices such as computer system 170 or sensor control device 102. Example data communication ports include USB ports, mini USB ports, USB Type-C ports, USB micro-A and/or micro-B ports, RS-232 ports, Ethernet ports, Firewire ports, or other similar data communication ports configured to connect to the compatible data cables. Reader device 120 may also include an integrated or attachable in vitro glucose meter, including an in vitro test strip port (not shown) to receive an in vitro glucose test strip for performing in vitro blood glucose measurements.

Reader device 120 can display the measured biometric data wirelessly received from sensor control device 102 and can also be configured to output alarms, alert notifications, glucose values, etc., which may be visual, audible, tactile, or any combination thereof. Further details and other display embodiments can be found in, e.g., U.S. Patent Publication No. 2011/0193704, which is incorporated herein by reference in its entirety for all purposes.

Reader device 120 can function as a data conduit to transfer the measured data from sensor control device 102 to computer system 170 or trusted computer system 180. In certain embodiments, the data received from sensor control device 102 may be stored (permanently or temporarily) in one or more memories of reader device 120 prior to uploading to system 170, 180 or network 190.

Computer system 170 may be a personal computer, a server terminal, a laptop computer, a tablet, or other suitable data processing device. Computer system 170 can be (or include) software for data management and analysis and communication with the components in analyte monitoring system 100. Computer system 170 can be used by the user or a medical professional to display and/or analyze the biometric data measured by sensor control device 102. In some embodiments, sensor control device 102 can communicate the biometric data directly to computer system 170 without an intermediary such as reader device 120, or indirectly using an internet connection (also optionally without first sending to reader device 120). Operation and use of computer system 170 is further described in the '225 Publication incorporated herein. Analyte monitoring system 100 can also be configured to operate with a data processing module (not shown), also as described in the incorporated '225 Publication.

Trusted computer system 180 can be within the possession of the manufacturer or distributor of sensor control device 102, either physically or virtually through a secured connection, and can be used to perform authentication of sensor control device 102, for secure storage of the user's biometric data, and/or as a server that serves a data analytics program (e.g., accessible via a web browser) for performing analysis on the user's measured data.

Example Embodiments of Reader Devices

Reader device 120 can be a mobile communication device such as a mobile telephone including, but not limited to, a Wi-Fi or internet enabled smart phone, tablet, or personal digital assistant (PDA). Examples of smart phones can include those mobile phones based on a Windows® operating system, Android™ operating system, iPhone® operating system, Palm® WebOS™, Blackberry® operating system, or Symbian® operating system, with data network connectivity functionality for data communication over an internet connection and/or a local area network (LAN).

Reader device 120 can also be configured as a mobile smart wearable electronics assembly, such as an optical assembly that is worn over or adjacent to the user's eye (e.g., a smart glass or smart glasses, such as Google glasses, which is a mobile communication device). This optical assembly can have a transparent display that displays information about the user's analyte level (as described herein) to the user while at the same time allowing the user to see through the display such that the user's overall vision is minimally obstructed. The optical assembly may be capable of wireless communications similar to a smart phone. Other examples of wearable electronics include devices that are worn around or in the proximity of the user's wrist (e.g., a watch, etc.), neck (e.g., a necklace, etc.), head (e.g., a headband, hat, etc.), chest, or the like.

Figure 1B:
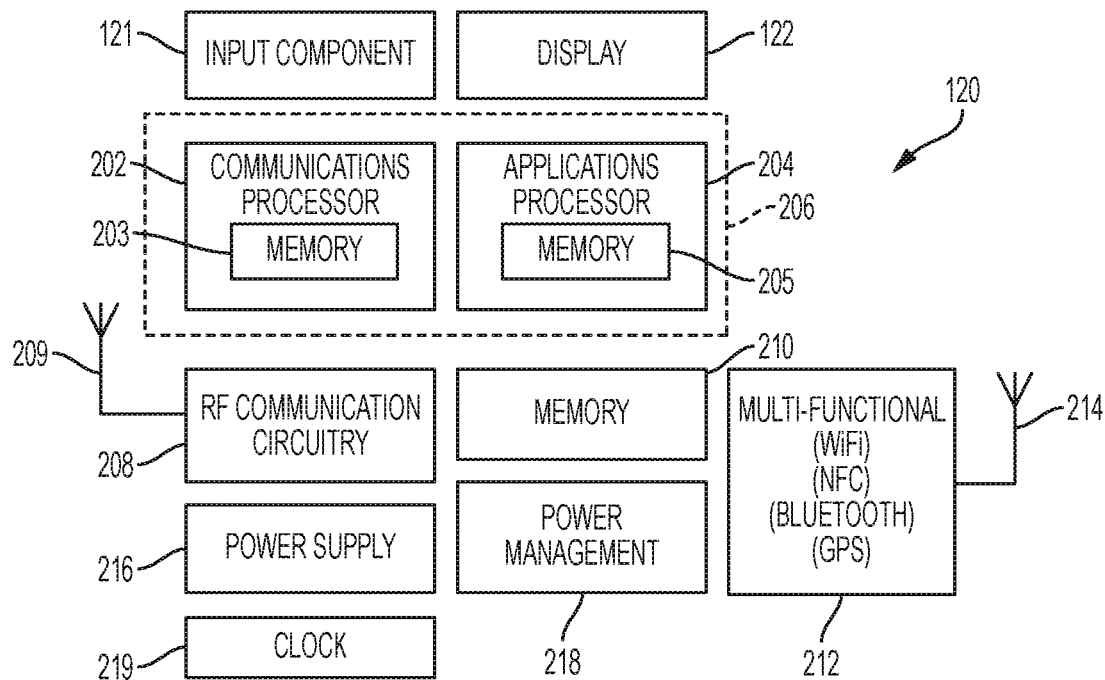
FIG. 1B is a block diagram of an example embodiment of a reader device.

FIG. 1B is a block diagram of an example embodiment of a reader device 120 configured as a smart phone. Here, reader device 120 includes an input component 121, display 122, and processing circuitry 206, which can include one or more processors, microprocessors, controllers, and/or microcontrollers, each of which can be a discrete chip or distributed amongst (and a portion of) a number of different chips. Here, processing circuitry 206 includes a communications processor 202 having on-board memory 203 and an applications processor 204 having on-board memory 205. Reader device 120 further includes RF communication circuitry 208 coupled with an RF antenna 209, a memory 210, multi-functional circuitry 212 with one or more associated antennas 214, a power supply 216, power management circuitry 218, and a clock 219. FIG. 1B is an abbreviated representation of the typical hardware and functionality that resides within a smart phone and those of ordinary skill in the art will readily recognize that other hardware and functionality (e.g., codecs, drivers, glue logic) can also be included.

Communications processor 202 can interface with RF communication circuitry 208 and perform analog-to-digital conversions, encoding and decoding, digital signal processing and other functions that facilitate the conversion of voice, video, and data signals into a format (e.g., in-phase and quadrature) suitable for provision to RF communication circuitry 208, which can then transmit the signals wirelessly. Communications processor 202 can also interface with RF communication circuitry 208 to perform the reverse functions necessary to receive a wireless transmission and convert it into digital data, voice, and video. RF communication circuitry 208 can include a transmitter and a receiver (e.g., integrated as a transceiver) and associated encoder logic.

Applications processor 204 can be adapted to execute the operating system and any software applications that reside on reader device 120, process video and graphics, and perform those other functions not related to the processing of communications transmitted and received over RF antenna 209. The smart phone operating system will operate in conjunction with a number of applications on reader device 120. Any number of applications (also known as "user interface applications") can be running on reader device 120 at any one time, and may include one or more applications that are related to a diabetes monitoring regime, in addition to the other commonly used applications that are unrelated to such a regime, e.g., email, calendar, weather, sports, games, etc. For example, the data indicative of a sensed analyte level and in vitro blood analyte measurements received by the reader device can be securely communicated to user interface applications residing in memory 210 of reader device 120. Such communications can be securely performed, for example, through the use of mobile application containerization or wrapping technologies.

Memory 210 can be shared by one or more of the various functional units present within reader device 120, or can be distributed amongst two or more of them (e.g., as separate memories present within different chips). Memory 210 can also be a separate chip of its own. Memories 203, 205, and 210 are non-transitory, and can be volatile (e.g., RAM, etc.) and/or non-volatile memory (e.g., ROM, flash memory, F-RAM, etc.).

Multi-functional circuitry 212 can be implemented as one or more chips and/or components (e.g., transmitter, receiver, transceiver, and/or other communication circuitry) that perform other functions such as local wireless communications, e.g., with sensor control device 102 under the appropriate protocol (e.g., Wi-Fi, Bluetooth, Bluetooth Low Energy, Near Field Communication (NFC), Radio Frequency Identification (RFID), proprietary protocols, and others) and determining the geographic position of reader device 120 (e.g., global positioning system (GPS) hardware). One or more other antennas 214 are associated with the functional circuitry 212 as needed to operate with the various protocols and circuits.

Power supply 216 can include one or more batteries, which can be rechargeable or single-use disposable batteries. Power management circuitry 218 can regulate battery charging and power supply monitoring, boost power, perform DC conversions, and the like.

Reader device 120 can also include or be integrated with a drug (e.g., insulin, etc.) delivery device such that they, e.g., share a common housing. Examples of such drug delivery devices can include medication pumps having a cannula that remains in the body to allow infusion over a multi-hour or multi-day period (e.g., wearable pumps for the delivery of basal and bolus insulin). Reader device 120, when combined with a medication pump, can include a reservoir to store the drug, a pump connectable to transfer tubing, and an infusion cannula. The pump can force the drug from the reservoir, through the tubing and into the diabetic's body by way of the cannula inserted therein. Other examples of drug delivery devices that can be included with (or integrated with) reader device 120 include portable injection devices that pierce the skin only for each delivery and are subsequently removed (e.g., insulin pens). A reader device 120, when combined with a portable injection device, can include an injection needle, a cartridge for carrying the drug, an interface for controlling the amount of drug to be delivered, and an actuator to cause injection to occur. The device can be used repeatedly until the drug is exhausted, at which point the combined device can be discarded, or the cartridge can be replaced with a new one, at which point the combined device can be reused repeatedly. The needle can be replaced after each injection.

The combined device can function as part of a closed-loop system (e.g., an artificial pancreas system requiring no user intervention to operate) or semi-closed loop system (e.g., an insulin loop system requiring seldom user intervention to operate, such as to confirm changes in dose). For example, the diabetic's analyte level can be monitored in a repeated automatic fashion by sensor control device 102, which can then communicate that monitored analyte level to reader device 120, and the appropriate drug dosage to control the diabetic's analyte level can be automatically determined and subsequently delivered to the diabetic's body. Software instructions for controlling the pump and the amount of insulin delivered can be stored in the memory of reader device 120 and executed by the reader device's processing circuitry. These instructions can also cause calculation of drug delivery amounts and durations (e.g., a bolus infusion and/or a basal infusion profile) based on the analyte level measurements obtained directly or indirectly from sensor control device 102. In some embodiments sensor control device 102 can determine the drug dosage and communicate that to reader device 120.

Example Embodiments of Sensor Control Devices

Figure 1C:
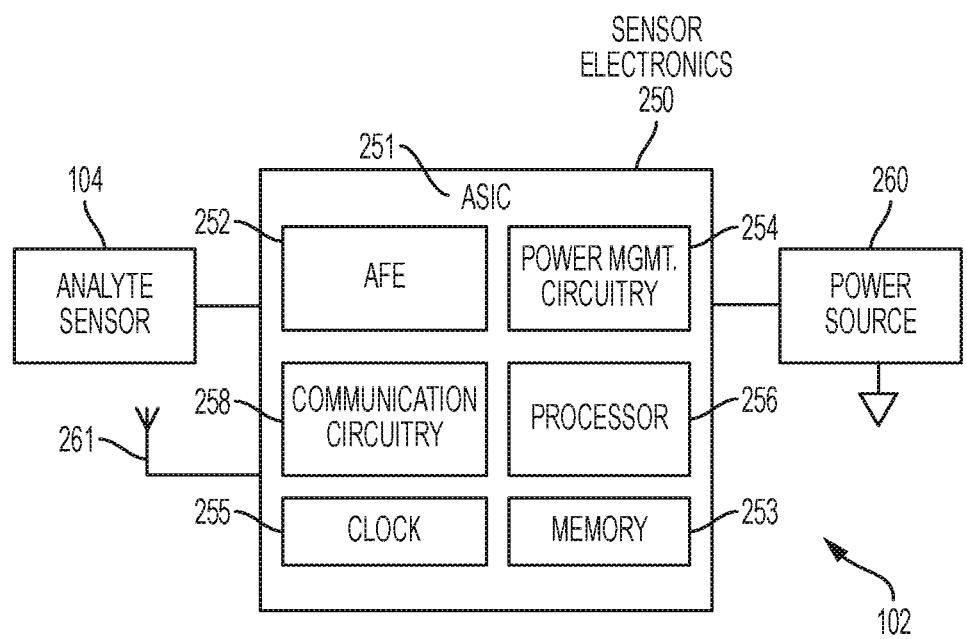
FIG. 1C is a block diagram depicting an example embodiment of sensor control device.

FIG. 1C is a block diagram depicting an example embodiment of sensor control device 102 having analyte sensor 104 and sensor electronics 250 (including analyte monitoring circuitry) that can have the majority of the processing capability for rendering end-result data suitable for display to the user. In FIG. 1C, a single semiconductor chip 251 is depicted that can be a custom application specific integrated circuit (ASIC). Shown within ASIC 251 are certain high-level functional units, including an analog front end (AFE) 252, power management (or control) circuitry 254, processor 256, and communication circuitry 258 (which can be implemented as a transmitter, receiver, transceiver, passive circuit, or otherwise according to the communication protocol). In this embodiment, both AFE 252 and processor 256 are used as analyte monitoring circuitry, but in other embodiments either circuit can perform the analyte monitoring function. Processor 256 can include one or more processors, microprocessors, controllers, and/or microcontrollers, each of which can be a discrete chip or distributed amongst (and a portion of) a number of different chips.

A memory 253 is also included within ASIC 251 and can be shared by the various functional units present within ASIC 251, or can be distributed amongst two or more of them. Memory 253 can also be a separate chip. Memory 253 is non-transitory and can be volatile and/or non-volatile memory. In this embodiment, ASIC 251 is coupled with power source 260, which can be a coin cell battery, or the like. AFE 252 interfaces with in vivo analyte sensor 104 and receives measurement data therefrom and outputs the data to processor 256 in digital form, which in turn can, in some embodiments, process in any of the manners described elsewhere herein. This data can then be provided to communication circuitry 258 for sending, by way of antenna 261, to reader device 120 (not shown), for example, where minimal further processing is needed by the resident software application to display the data. Antenna 261 can be configured according to the needs of the application and communication protocol. Antenna 261 can be, for example, a printed circuit board (PCB) trace antenna, a ceramic antenna, or a discrete metallic antenna. Antenna 261 can be configured as a monopole antenna, a dipole antenna, an F-type antenna, a loop antenna, and others.

Information may be communicated from sensor control device 102 to a second device (e.g., reader device 120) at the initiative of sensor control device 102 or reader device 120. For example, information can be communicated automatically and/or repeatedly (e.g., continuously) by sensor control device 102 when the analyte information is available, or according to a schedule (e.g., about every 1 minute, about every 5 minutes, about every 10 minutes, or the like), in which case the information can be stored or logged in a memory of sensor control device 102 for later communication. The information can be transmitted from sensor control device 102 in response to receipt of a request by the second device. This request can be an automated request, e.g., a request transmitted by the second device according to a schedule, or can be a request generated at the initiative of a user (e.g., an ad hoc or manual request). In some embodiments, a manual request for data is referred to as a "scan" of sensor control device 102 or an "on-demand" data transfer from device 102. In some embodiments, the second device can transmit a polling signal or data packet to sensor control device 102, and device 102 can treat each poll (or polls occurring at certain time intervals) as a request for data and, if data is available, then can transmit such data to the second device. In many embodiments, the communication between sensor control device 102 and the second device are secure (e.g., encrypted and/or between authenticated devices), but in some embodiments the data can be transmitted from sensor control device 102 in an unsecured manner, e.g., as a broadcast to all listening devices in range.

Different types and/or forms and/or amounts of information may be sent as part of each communication including, but not limited to, one or more of current sensor measurements (e.g., the most recently obtained analyte level information temporally corresponding to the time the reading is initiated), rate of change of the measured metric over a predetermined time period, rate of the rate of change of the metric (acceleration in the rate of change), or historical metric information corresponding to metric information obtained prior to a given reading and stored in a memory of sensor control device 102.

Some or all of real time, historical, rate of change, rate of rate of change (such as acceleration or deceleration) information may be sent to reader device 120 in a given communication or transmission. In certain embodiments, the type and/or form and/or amount of information sent to reader device 120 may be preprogrammed and/or unchangeable (e.g., preset at manufacturing), or may not be preprogrammed and/or unchangeable so that it may be selectable and/or changeable in the field one or more times (e.g., by activating a switch of the system, etc.). Accordingly, in certain embodiments reader device 120 can output a current (real time) sensor-derived analyte value (e.g., in numerical format), a current rate of analyte change (e.g., in the form of an analyte rate indicator such as an arrow pointing in a direction to indicate the current rate), and analyte trend history data based on sensor readings acquired by and stored in memory of sensor control device 102 (e.g., in the form of a graphical trace). Additionally, an on-skin or sensor temperature reading or measurement may be communicated from sensor control device 102 with each data communication. The temperature reading or measurement, however, may be used in conjunction with a software routine executed by reader device 120 to correct or compensate the analyte measurement output to the user, instead of or in addition to actually displaying the temperature measurement to the user.

Example Embodiments of RF Redirectors

Fixed position transmitter and receiver pairs can optimize their antennas in a direct line of sight to maximize transmission efficiency. This stems from the fact that these pairs can be properly aligned when mounting in their fixed positions. On the other hand, wearable on body devices that communicate with other devices need to accommodate transmissions in a number of different directions given the moving, unfixed nature of these systems. On body devices that can transmit in multiple directions, or that can transmit in an omnidirectional manner, increase the likelihood that the transmitted signal will be received if the direct path between transmitter and receiver is partially or entirely blocked, as compared to on body devices that transmit in a relatively smaller number of directions, or in only one direction. Because the transmission occurs in a greater number of directions, there is a greater chance that it can be indirectly received after, for example, reflecting off a feature in the immediate environment (e.g., walls, floors, ceilings, furniture, etc.). Therefore, in some cases, it may be desirable to improve the transmission and reception performance of an on body device, such as sensor control device 102.

Example embodiments of secondary communication systems are described herein that allow for the capture of RF signals transmitted by an on body device and retransmission of those RF signals in a relatively greater number of directions. In many of these embodiments the secondary communication system takes the form of an RF redirection device. The RF redirection device can be completely passive, such that no additional power supply is required. These embodiments are particularly useful in modifying or retrofitting an existing on body device that has only a single or limited number of antennas transmitting and/or receiving in only a single or limited number of directions. For example, because on body devices often have a relatively small form factor, the available space within the device is constrained. Thus, the device may have a relatively small antenna that is constrained in the number of directions in which it can transmit or receive, e.g., the on body device does not transmit a balanced omnidirectional signal.

These example embodiments will be described in the context of a sensor control device 102 adapted to perform in vivo analyte measurements. However, as noted herein, these embodiments can be employed with a vast range of different on body devices, with or without analyte sensing capability.

Figure 2A:
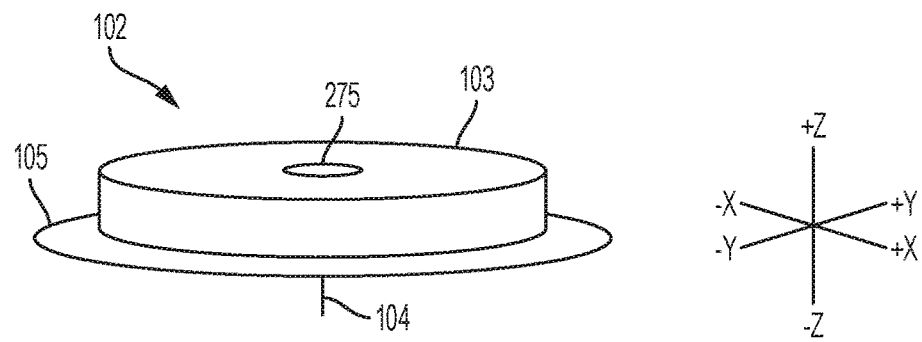
FIGS. 2A and 2B are a perspective view and side view, respectively, depicting an example embodiment of sensor control device.
Figure 2B:
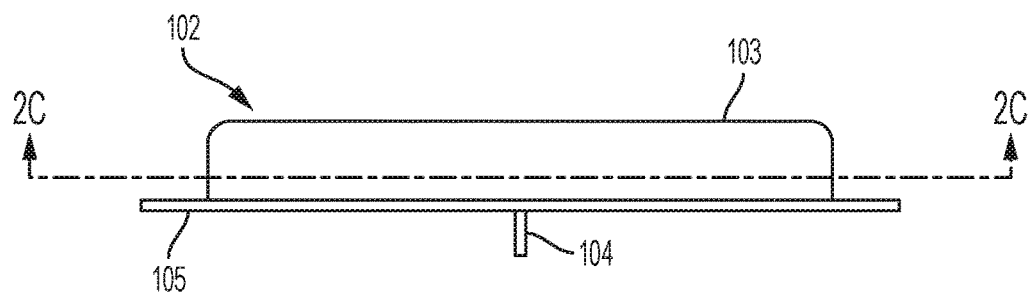

FIGS. 2A and 2B are a perspective view and side view, respectively, depicting an example embodiment of sensor control device 102 with housing 103 and adhesive pad 105. In vivo analyte sensor 104 can also be seen at bottom. Housing 103 can hold sensor electronics 250, an end of sensor 104, and a power source 260.

Figure 2C:
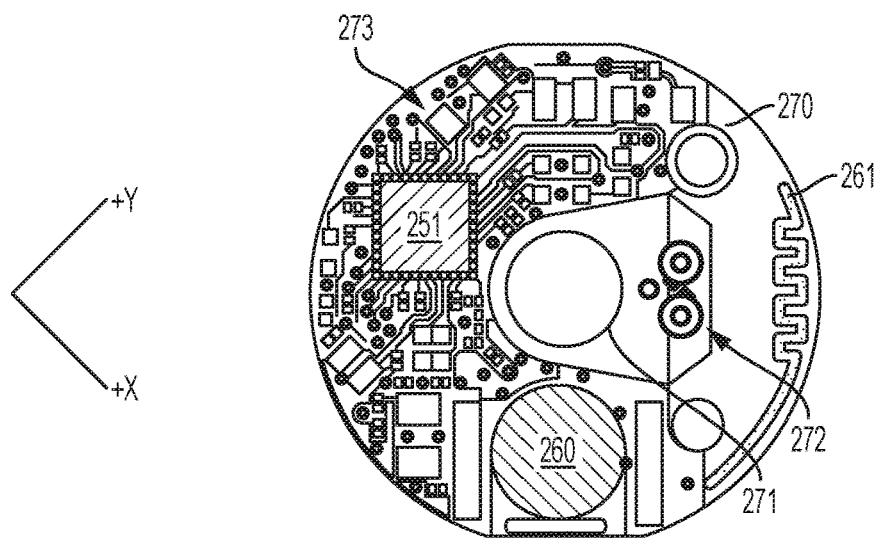
FIG. 2C is bottom up view of an example embodiment of a printed circuit board (PCB) as viewed from line 2C-2C of FIG. 2B.

FIG. 2C is bottom up view of a printed circuit board (PCB) 270 as viewed from line 2C-2C of FIG. 2B. PCB 270 can include conductive contacts for connection to various electronic components and can include conductive traces that form interconnections therebetween. Here, PCB 270 is coupled with ASIC 251, power source 260, various discrete electrical components 273 (e.g., resistors, capacitors, inductors, diodes, transistors, and the like). An aperture 271 extends through PCB 270 and can allow the passage of sensor 104 and a sharp (both not shown). PCB 270 includes electrical contacts 272 for connection with corresponding electrical contacts of sensor 104 (not shown). The conductive traces between these various components are not shown for ease of illustration.

In this embodiment, sensor control device 102 is configured to communicate with a second device (e.g. reader device 120) over a Bluetooth or BTLE wireless link. Antenna 261 is adapted for the transmission and reception of RF energy or signals in the Bluetooth or BTLE spectrum (e.g., 2.44 Gigahertz). Antenna 261 is implemented here as a conductive trace in or on PCB 270. Antenna 261 is curved in a manner corresponding to the curvature of the edge of PCB 270 and has a length selected or tuned to achieve transmission and reception on the desired frequency. All of the transmissions described herein as emanating from sensor control device 102, and being received by sensor control device 102 (e.g. such as transmissions from reader device 120), can be accomplished by use of antenna 261.

However, in this example antenna 261 is a single antenna and therefore has limited transmission strength in all various directions from sensor control device 102. For example, depending on the orientation of antenna 261, a limited amount of RF energy can be propagated from and received by antenna 261 in each of the X, Y, and Z directions indicated in FIG. 2A as compared to a device with multiple antennas.

Example embodiments described herein provide for RF redirection devices that can modify and improve the three-dimensional spatial coverage of the RF communication circuitry of the on body device. The main antenna 261 of an unmodified on body device transmits (and receives) in a first pattern within three-dimensional space, such as through the X-Y-Z coordinate system depicted in FIG. 2A. That first pattern can vary between implementations. In some examples, the first pattern exhibits the greatest transmission signal strength substantially along the Z direction, with relatively less strength along the X and Y directions. In other examples, the first pattern can exhibit the greatest transmission signal strength substantially along the X and/or Y directions, with a relatively lesser strength along the Z direction.

The RF redirection devices can be combined or integrated with the on body device, or otherwise used to modify or supplement the on body device such that: (a) RF signals transmitted by a main antenna of the on body device in the first pattern are captured with one or more primary antennas of the redirection device and then retransmitted using one or more secondary antennas of the redirection device in a second pattern, where the second pattern has a relatively greater transmission signal strength in at least a first direction (X, Y, and/or Z) as compared to the first pattern's transmission signal strength in that same first direction; and (b) RF signals transmitted by a second device to the on body device can be received or captured by the redirection device across the second pattern by the one or more secondary antennas and retransmitted by the one or more primary antennas to the main antenna of the on body device.

For example, the first pattern of the unmodified on body device may exhibit the greatest transmission strength along the Z direction, along with a substantially smaller strength in the X and Y directions. After combination of the on body device with the RF redirection device, the combined device may, in some examples, transmit in a second pattern that exhibits a transmission strength that is substantially the same as that of the unmodified device along the Z direction, but is greater than the unmodified device in at least the X direction (e.g., the first direction) and, in some cases, greater in the Y direction as well (e.g., a second direction). Other examples also exist. For instance, an unmodified on body device can have a first pattern where transmission occurs only along the Z direction and not in the X and Y directions (e.g., a uni-directional transmission pattern), but after combination with the RF redirection device, the combined device can have a second pattern where transmission occurs in all directions in X, Y, and Z space (e.g., an omni-directional pattern).

Embodiments of RF redirection device can be configured to capture RF signals transmitted by at least one main antenna of an on body device using at least one primary antenna. The primary antenna can be communicatively coupled with at least one secondary antenna that can re-transmit the RF signals in a different directional pattern. In all embodiments described herein, the primary and secondary antennas can be the same type of antenna as the main antenna (e.g., PCB trace, ceramic, monopole, dipole, etc.) or they can be different from the main antenna. In some embodiments, the primary antenna is the same as the main antenna and the at least one secondary antenna is different from the primary antenna.

Figure 3:
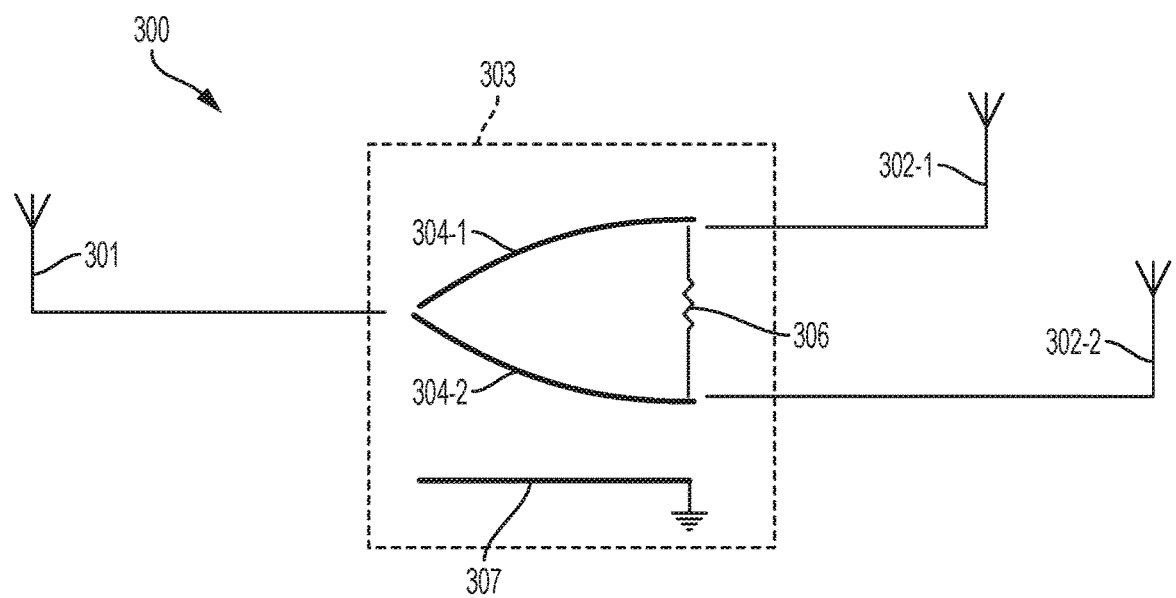
FIG. 3 is a schematic diagram depicting an example embodiment of an RF redirection device.

FIG. 3 is a schematic diagram depicting an example embodiment of an RF redirection device 300 that is configured to capture RF signals transmitted by a main antenna 261 of sensor control device 102 using primary antenna 301 and to re-transmit those RF signals using two secondary antennas 302-1 and 302-2. RF redirection device 300 can be a purely passive device that is not connected to nor otherwise relying upon a discrete power source to power its transmission and receipt of RF signals. The power of the received RF signal is captured and redirected. However, in other embodiments device 300 can be an active device and utilize a power source (e.g., a battery connected via a wire or conductive trace) to assist in transmission or reception.

RF signals captured by primary antenna 301 can be output to secondary antennas 302 in a number of different ways. For example, primary antenna 301 can direct the received signal to an RF power divider circuit 303. In this embodiment, RF power divider circuit 303 is an implementation of a Wilkinson power divider, although in other embodiments different implementations can be employed. RF power divider circuit 303 can include two traces 304-1 and 304-2 that can each be tuned to one-quarter wavelength of the received signal (e.g., 2.44 Ghz for BTLE, other frequencies for other protocols). Traces 304 can be surrounded by a conductive area coupled to an optional ground node or plane 307 such that they form coplanar transmission lines. A resistive element 306 is present between traces 304-1 and 304-2 to decouple them. The magnitude of resistance for resistive element 306 can be selected to prevent leakage or crosstalk between secondary antennas 302-1 and 302-2. Conductive trace 304-1 is then connected with secondary antenna 302-1 and conductive trace 304-2 is then connected with secondary antenna 302-2. Secondary antennas 302-1 and 302-2 can be oriented along different axes, such as perpendicular or orthogonal axes (e.g., X-axis and Y-axis). In this manner, the RF signal captured by primary antenna 301 can be split and redirected equally (or substantially equally) to secondary antennas 302-1 and 302-2, where the RF signal can be retransmitted along the two different axes to improve the directionality of transmission.

Figure 4A:
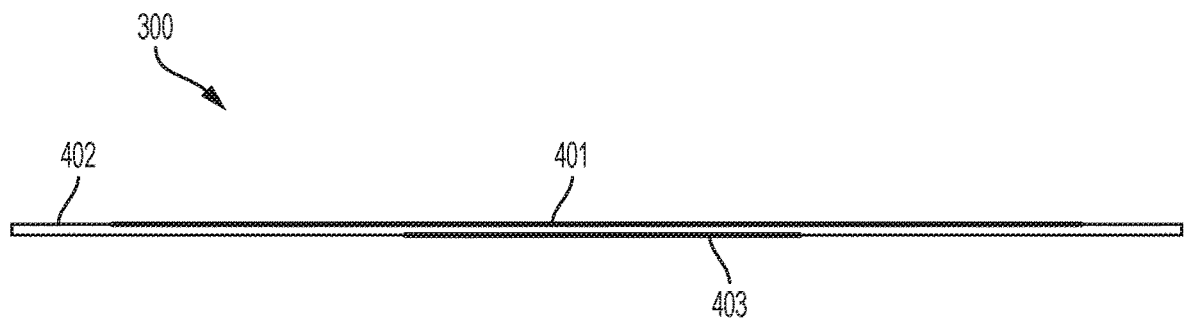
FIG. 4A is a side view depicting another example embodiment of an RF redirector device.

FIG. 4A is a side view depicting an example embodiment of RF redirector device 300 configured as a flexible attachment or patch. As can be seen here, device 300 has a first or upper layer 401 positioned on a substrate 402. Device 300 also includes a second or lower layer 403 on an opposite surface of substrate 402. In this embodiment, upper layer 401 includes primary antenna 301, secondary antennas 302, and RF power divider 303 (with the exception of ground plane 307), while lower layer 403 includes (or constitutes) ground plane 307. A number of manufacturing implementations can be used. In this embodiment, upper layer 401 and lower layer 403 can each be a conductive layer printed on a flexible PCB substrate 402.

Figure 4B:
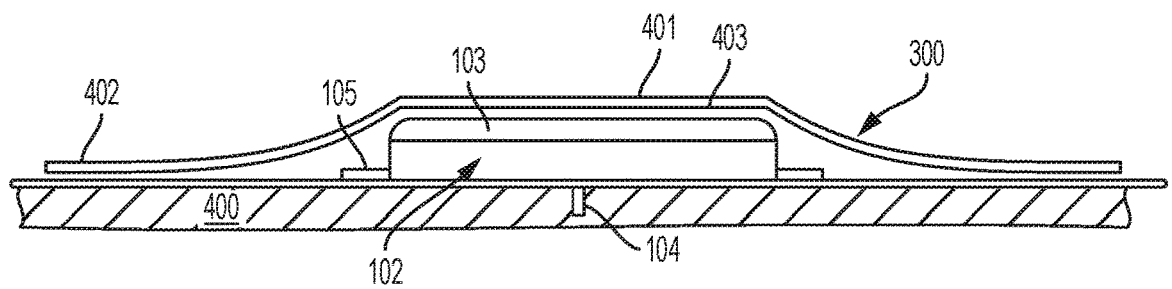
FIG. 4B is a partial cross-sectional view depicting another example embodiment of an RF redirection device attached to a sensor control device, which is in turn positioned on the body of a user.

Device 300 can be attached to sensor control device 102 that can be positioned on the body or clothes of a user, or otherwise carried by the user. FIG. 4B is a partial cross-sectional view depicting an example embodiment of device 300 positioned on sensor control device 102, and both are in turn attached to the user's skin 400. Sensor control device 102 can be adhesively attached to the user's skin 400 with adhesive pad 105. Analyte sensor 104 is shown partially positioned within the user's body. To facilitate the attachment of device 300 in the manner shown here, and adhesive can be present on the underside of substrate 402 and/or lower layer 403. Other manners of attachment can also be employed.

Figure 4C:
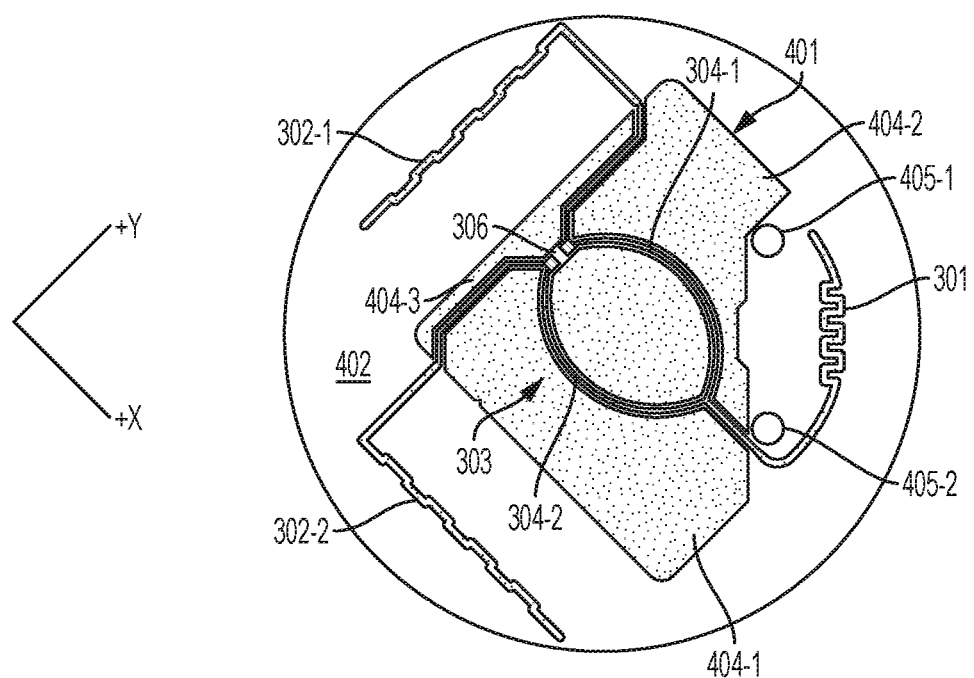
FIG. 4C is a top down view depicting an example embodiment of an upper layer configured as a conductive layer printed on or otherwise attached to a substrate.

FIG. 4C is a top down view depicting an example embodiment of upper layer 401 configured as a conductive layer printed on or otherwise attached to substrate 402. Upper layer 401 can be positioned on substrate 402 in a predetermined fashion with respect to one or more alignment features such as the circular indicators 405-1 and 405-2 depicted here.

In this embodiment, primary antenna 301 is shaped generally in the same manner as antenna 261 of sensor control device 102 as depicted in FIG. 2C such that antenna 301 is matched to antenna 261 to maximize the amount of RF energy captured by primary antenna 301. Antenna 301 is connected to conductive traces 304-1 and 304-2, which are in turn connected to secondary antennas 302-1 and 302-2. In some embodiments, primary antenna 301, traces 304, and antennas 302 are all formed from a single contiguous layer of conductive material (e.g., a metal such as copper). Resistor 306 can be implemented in a number of different manners, for example, resistor 306 can be a carbon ink resistor, a semiconductor resistor, a ceramic resistor, or others. One or more planar conductive regions 404 (in this embodiment three planar regions 404-1, 404-2, and 404-3) can be used to substantially surround and shield the traces 304 of RF divider 303. In this embodiment, antennas 301 and 302 have a stepped or serpentine shape to adjust the antenna length to assist in frequency tuning.

Here, primary antenna 301 is curved and extends in both the X and Y directions, while secondary antenna 302-1 extends in substantially only the Y direction and secondary antenna 302-2 extends in substantially only the X direction, such that the antennas 302 are perpendicular or orthogonal to each other. Secondary antennas 302-1 and 302-2 also have a transverse orientation with respect to primary antenna 301 (e.g., a generally 45 degree offset here) and likewise the main antenna 261 when aligned with primary antenna 301. Placement of secondary antennas 302 at an orthogonal angle to each other and also at a transverse orientation to the primary and main antennas increases the number of directions in which device 300 can transmit as compared to main antenna 261 alone. In many cases, primary antenna 301 does not capture all of the signal propagated by main antenna 261 and thus the remaining uncaptured fraction of the signal is propagated into free space where it forms part of the directional transmission pattern and can be received by the second device. In other embodiments, three or more secondary antennas 302 can be present at various locations about the periphery of layer 401. In one example embodiment, an additional secondary antenna 302 is provided outside of layer 401 and oriented along the longitudinal z-axis.

Figure 4D:
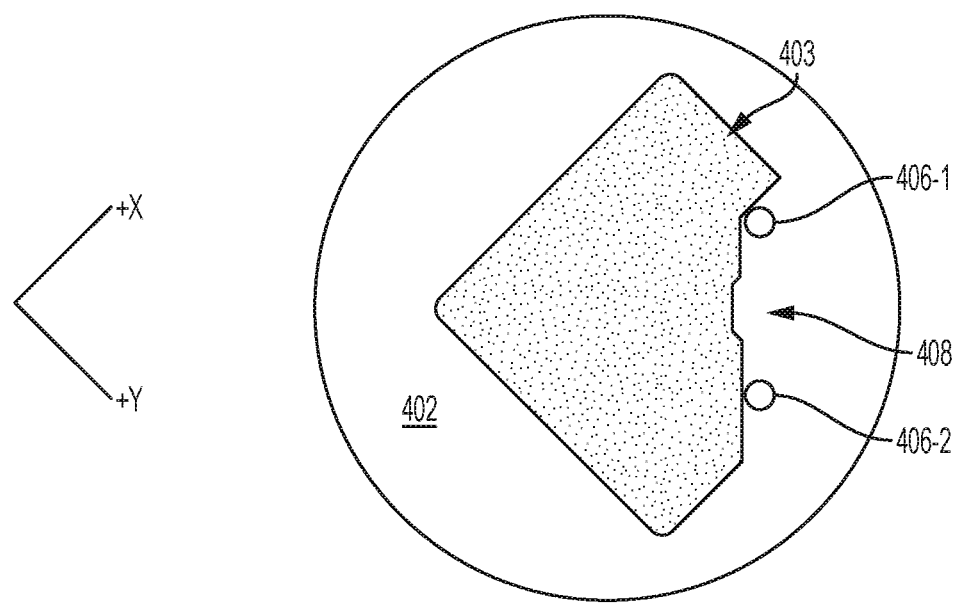
FIG. 4D is a bottom-up view depicting an example embodiment of a lower layer configured as a conductive layer printed on or otherwise attached to a substrate.

FIG. 4D is a bottom-up view depicting an example embodiment of lower layer 403 configured as a conductive layer printed on or otherwise attached to substrate 402. Lower layer 403 has a profile or shape that matches or corresponds to the outer profile of upper layer 401, specifically in this embodiment along the outermost edge of planar regions 404. Lower layer 403 is configured to act as a ground plane or node that shields RF power divider 303 from interference generated by the electronics 250 and antenna 261 of sensor control device 102. An open region 408 is present in the location directly beneath antenna 301 of upper layer 401 to permit the RF signal from antenna 261 to pass lower layer 403 relatively unimpeded such that it can be captured by antenna 301. Substrate 402 includes indicators 406-1 and 406-2 to assist in fabricating lower layer 403 on substrate 402 in the proper position and/or to assist in placement of device 300 over sensor control device 102 in the proper orientation (e.g. where antenna 301 is aligned directly over antenna 261 (in the Z direction). In some embodiments, indicators 405-1 and 406-1 are formed by the same structure or through a hole in substrate 402, and likewise for indicators 405-2 and 406-2. When RF redirector device 300 is applied to sensor control device 102, the position of the indicators 405 and/or 406 are preferably matched to the position of one or more other indicators on the on body device to achieve proper alignment of primary antenna 301 with main antenna 261.

Figure 4E:
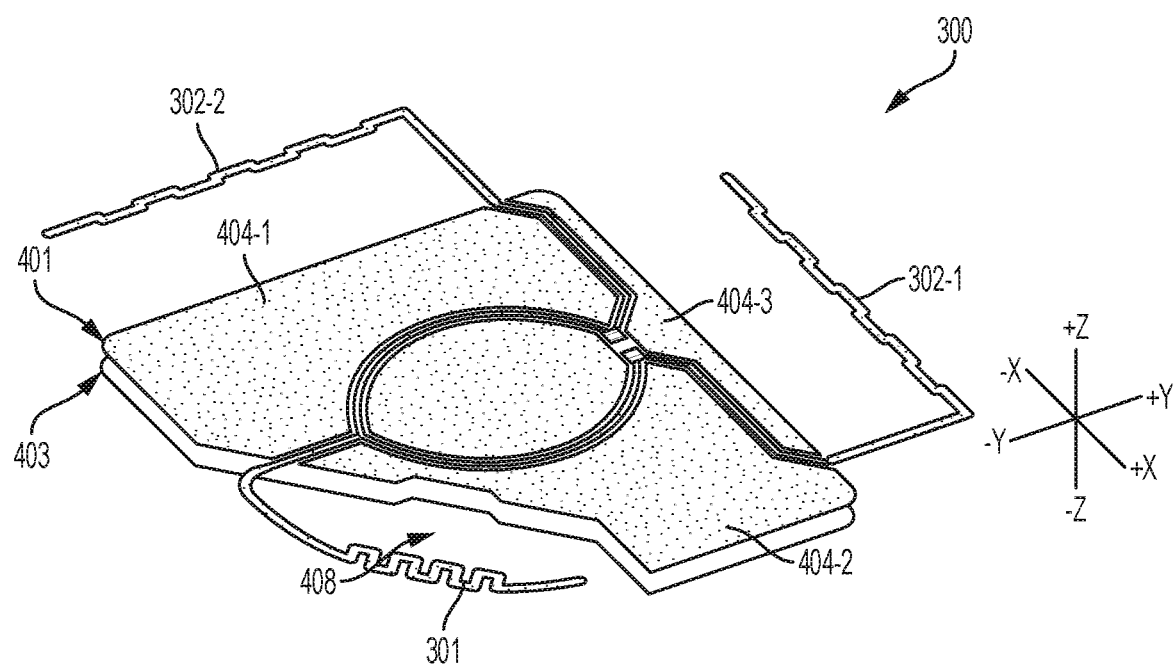
FIG. 4E is a perspective view depicting another example embodiment of an RF redirector device.

FIG. 4E is a perspective view depicting an example embodiment of RF redirector device 300, specifically showing layers 401 and 403 with substrate 402 omitted for clarity. As can be seen here, the unshielded region 408 of lower layer 403 is directly beneath primary antenna 301 so as not to attenuate the RF signal transmitted by antenna 261 to antenna 301 nor the RF signal transmitted by antenna 301 to antenna 261.

Figure 5A:
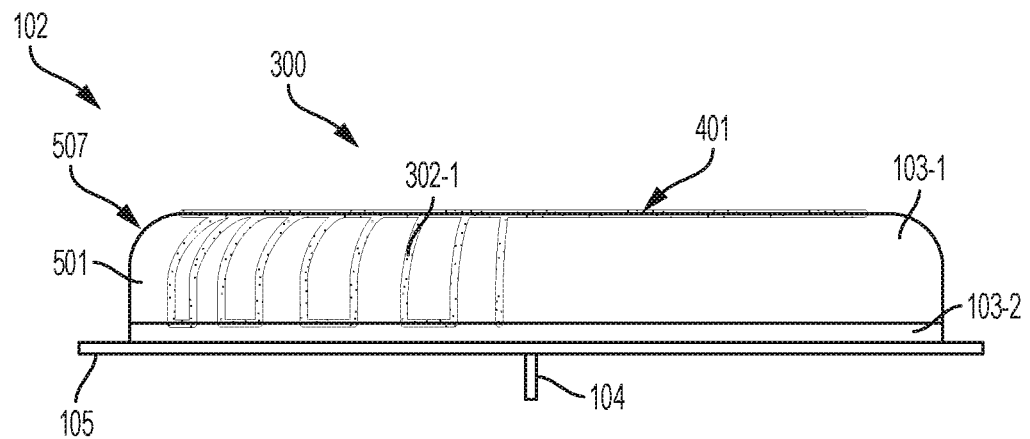
FIG. 5A is a side view depicting an example embodiment of a sensor control device.

As an alternative to the flexible patch configuration, RF redirector device 300 can be located on or in the housing 103 of sensor control device 102. Housing 103 can include one or more housing components. FIG. 5A is a side view of sensor control device 102 where housing 103 includes a first upper portion 103-1 and a second lower portion 103-2. These portions 103 can be coupled together in a multitude of ways, such as with the use of adhesive, with use of a clip or detent and corresponding groove, with a threaded interface, welding, and the like. In this embodiment, upper portion 103-1 has upper layer 401 located on an exterior surface thereof. The majority of upper layer 401 is located on the top surface of upper housing 103-1 while the secondary antennas 302 extend downwards from the top surface, over an edge region 507, and along all or part of an exterior surface of a side wall 501 of upper housing 103-1. Secondary antenna 302-1 can be seen here extending downwards alongside wall 501 to the base of upper housing portion 103-1.

Figure 5B:
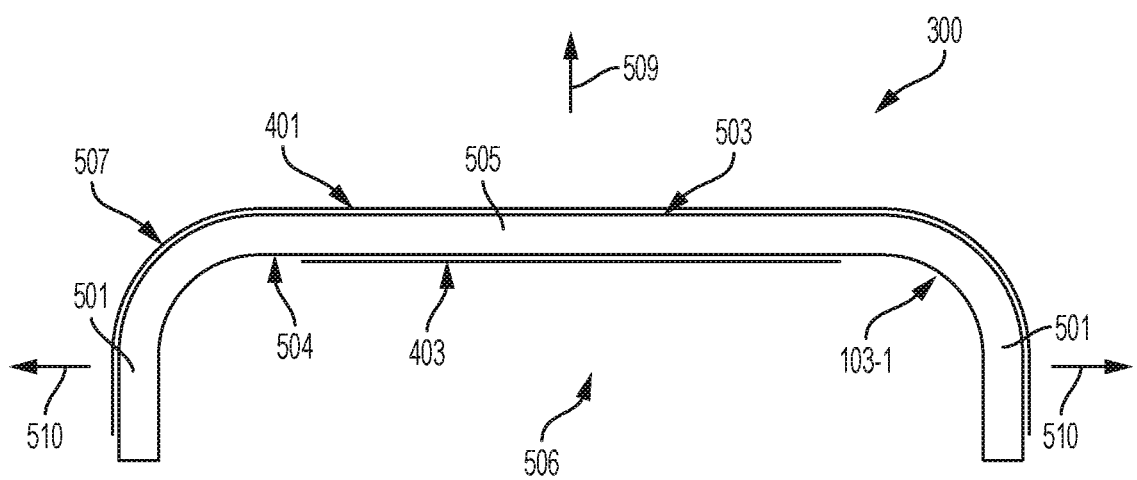
FIG. 5B is a partial cross-sectional view depicting another example embodiment of an RF redirector device.

FIG. 5B is a partial cross-sectional view depicting an example embodiment of device 300 located on upper housing portion 103-1. Here, upper layer 401 is located on exterior surface 503 of upper housing portion 103-1 extending along top wall 505 and sidewalls 501 of upper housing portion 103-1. One or both of secondary antennas 302 can be positioned along side wall 501 to increase the RF directional performance of device 102, particularly in the lateral directions 510 radiating outwards from the sides of device 102 (as compared to the longitudinal or vertical direction 509 shown here). Secondary antennas 302 can be positioned entirely on side wall 501 or partially along side wall 501 and partially along top wall 503. In this embodiment, upper housing portion 103-1 is configured such that it has a concavity (e.g., as a case or dome etc.) that creates an interior space 506 in which one or more components of device 102 can be housed. Lower layer 403 can be located on an interior surface 504 of upper housing portion 103-1 adjacent interior space 506. In this embodiment, lower layer 503 extends along top wall 505 but not side wall 501. As with the embodiments described with respect to FIGS. 4A-E, primary antenna 301 (not shown) can be placed directly over antenna 261 (not shown) unobstructed by lower layer 403.

Figure 5C:
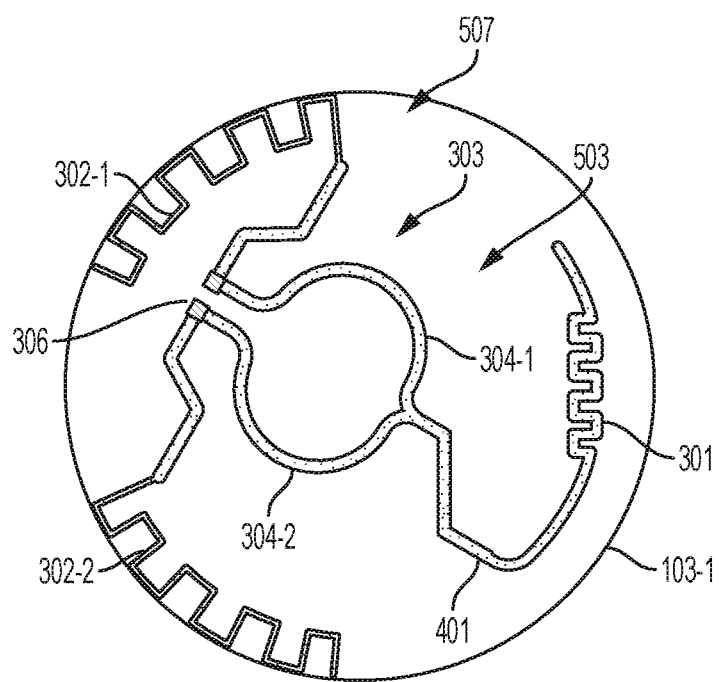
FIG. 5C is a top down view depicting an example embodiment of an upper housing having a top layer located on an upper exterior surface.

FIG. 5C is a top down view of upper housing portion 103-1 having top layer 401 located on upper exterior surface 503. As shown here, primary antenna 301 is generally on the top of upper housing portion 103-1 and secondary antennas 302-1 and 302-2 are located partially on top, extending over the edge, and generally down the sides of upper housing portion 103-1. Also shown here are the various components of device 300, including power divider 303 with waveguides 304, and resistor 306.

Figure 5D:
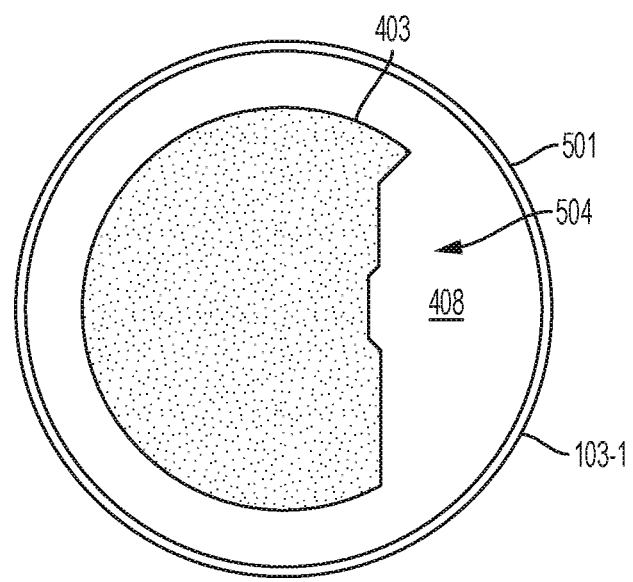
FIG. 5D is a bottom up view depicting an example embodiment of an upper housing portion having a bottom layer located on an interior surface.

FIG. 5D is a bottom up view of upper housing portion 103-1 having bottom layer 403 located on interior surface 504. Open region 408 is visible in a location generally beneath the position of primary antenna 301 (not shown). The base edge of sidewall 501 is also visible.

Figure 6A:
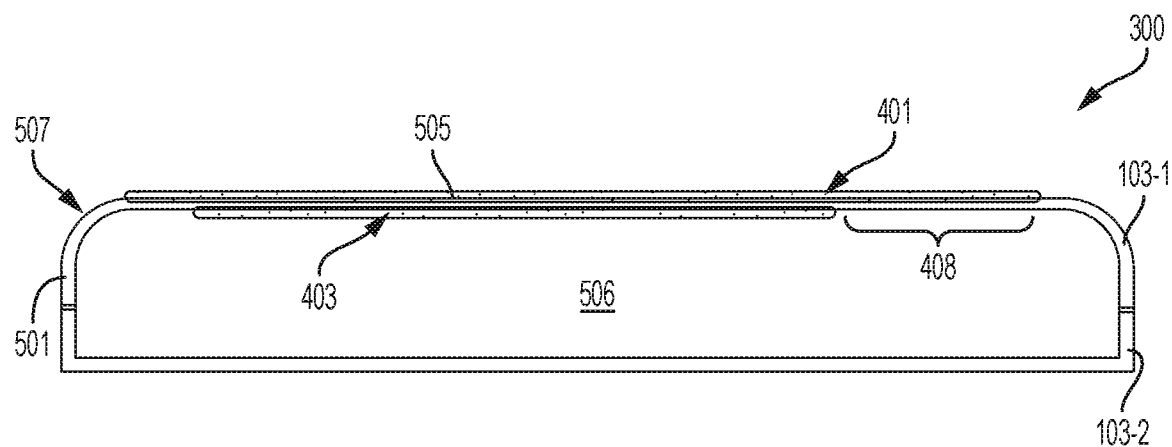
FIG. 6A is a partial cross-sectional view depicting an example embodiment of an upper housing portion secured to a lower housing portion.
Figure 6B:
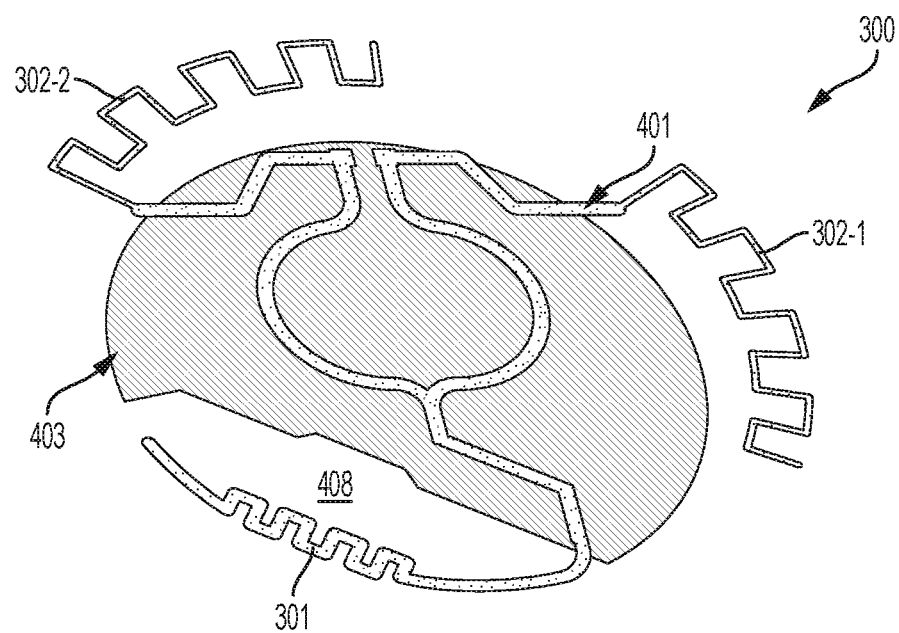
FIG. 6B is a perspective view depicting the embodiment of FIG. 6A.

Another example embodiment of device 300 is depicted in FIGS. 6A-B. FIG. 6A is a partial cross-sectional view of upper housing portion 103-1 secured to lower housing portion 103-2. Here, upper layer 401 is located only along top wall 505 and does not extend downward over the upper edge region nor along sidewall 501. Lower layer 403 is again positioned on interior surface 504 of top wall 505 with the position of open region 408 indicated. FIG. 6B is a perspective view depicting the embodiment of FIG. 6A, particularly the relative orientation of layer 401 with respect to layer 403. Top wall 505 is omitted for clarity.

In the example embodiments described herein, layers 401 and 403 are described as being positioned on a substrate, such as substrate 402 and housing 103. Layers 401 and 403 can be positioned on those substrates using any number of manufacturing techniques including, but not limited to, printing, masking, insert molding, and others. In addition, layers 401 and/or 403 are not required to be on an exterior or interior surface of device 102, and can instead be encapsulated within, under a coating, or within a lamination of device 102. Furthermore, layers 401 and 403 are not required to be fabricated as layers, but rather each layer 401 and 403 can be formed from discrete components subsequently assembled together.

Figure 7A:
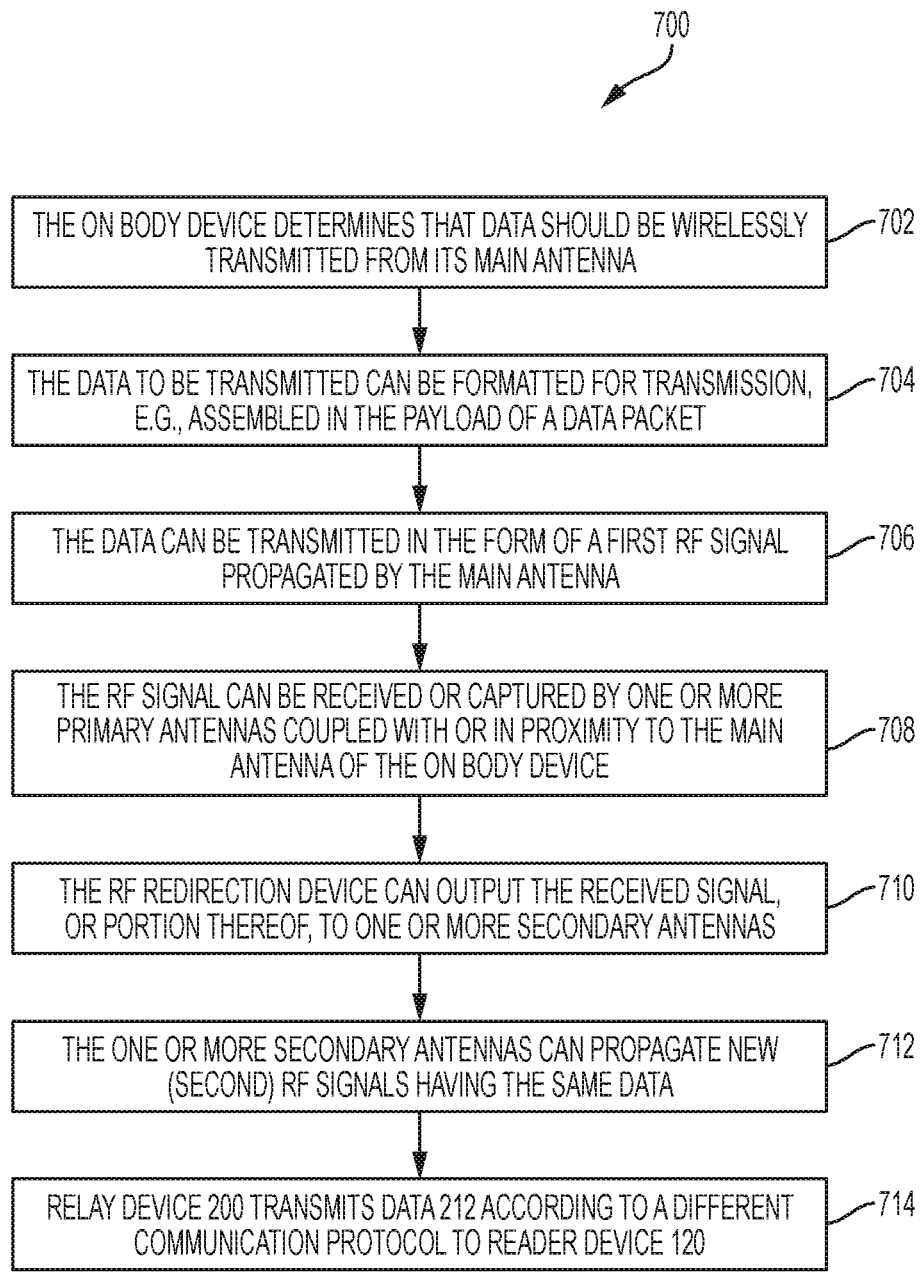
FIGS. 7A-B are flow diagrams depicting example embodiments of methods of using an RF redirection device with an on body device.

FIG. 7A is a flow diagram depicting an example embodiment of a method 700 of using RF redirection device 300 with an on body device to accomplish a data transmission. By way of example, specific references are made to the operation of device 300 within analyte monitoring system 100, although the use of device 300 is not limited to such. At 702, the on body device (e.g., sensor control device 102) determines that data should be wirelessly transmitted from its main antenna (e.g., antenna 261). As described elsewhere herein, the determination that a transmission should occur can be for a number of reasons, such as the receipt of a request for data or poll signal from a second device (e.g., reader device 120, a relay device, a drug delivery device, etc.), the collection of new data by a sensor of the on body device, the expiration of a predetermined amount of time since the last data transmission from the on body device, the performance of an initiation routine such as that which may occur after initial activation of the on body device, the arrival at a scheduled point in time for transmission, and the like.

At 704, the data to be transmitted can be formatted for transmission, e.g., assembled in the payload of a data packet. At 706, the data can be transmitted in the form of a first RF signal propagated by the main antenna 261. Then, at 708, this RF signal can be received or captured by one or more primary antennas 301 of RF redirection device 300 coupled with or in proximity to the main antenna 261 of the on body device 102. At 710, RF redirection device 300 can output the received signal, or a portion thereof, to one or more secondary antennas 302. This can occur, in some embodiments, by use of an RF power divider or RF power splitter to assign the desired portion of the received signal to each of the one or more secondary antennas 302. In the embodiments described herein, RF power divider 303 splits power generally equally between two secondary antennas 302. In other embodiments, the RF power can be divided unequally such that a first, relatively greater fraction or amount is supplied to a first secondary antenna 302 and the second, relatively lesser fraction or amount is supplied to a second secondary antenna 302. Upon receipt of the signal originally received by primary antenna 301, then at 712, the one or more secondary antennas 302 can propagate new (second) RF signals having the same data. These new RF signals can be transmitted in a different directional pattern than the first RF signal originally transmitted by the main antenna 261 of the on body device 102. These new RF signals can be transmitted at the same frequency as that signal originally transmitted by the main antenna 261 or, in other embodiments, these new RF signals can be transmitted at different frequencies if desired.

Figure 7B:
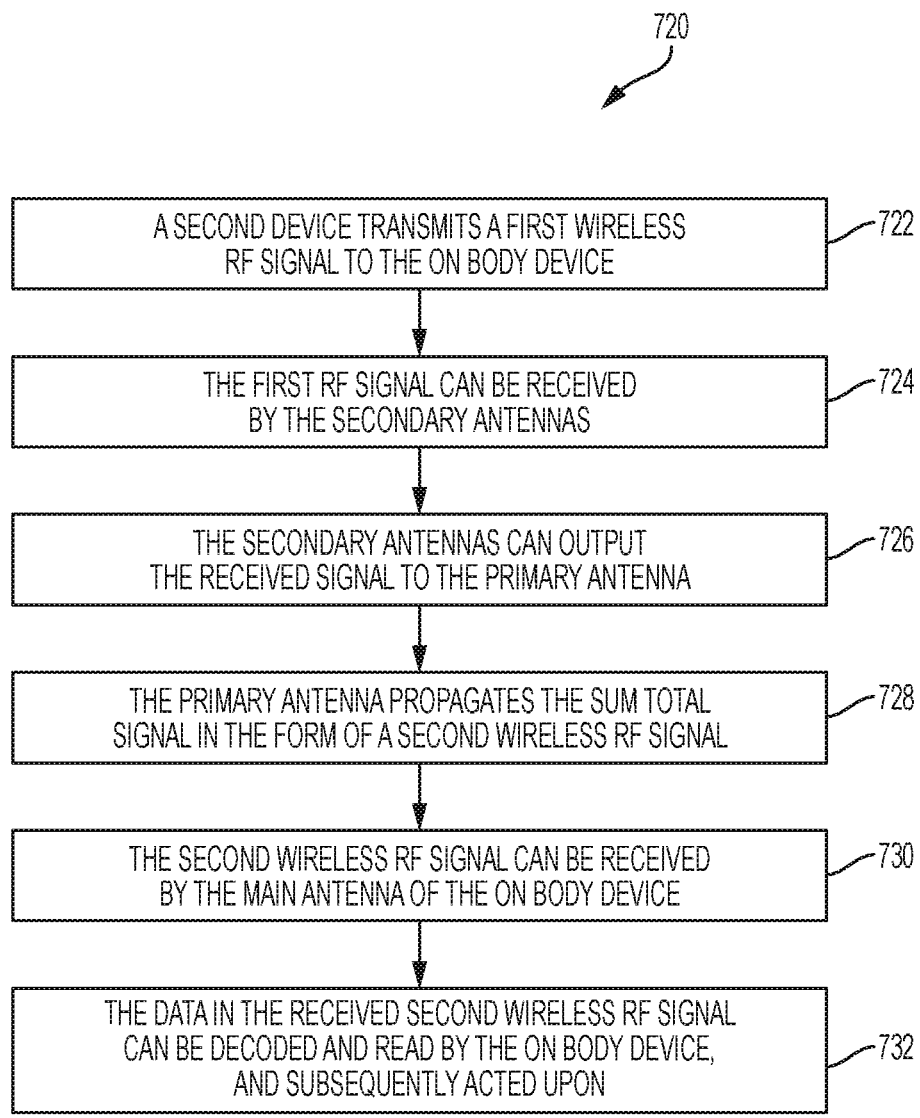

FIG. 7B is a flow diagram depicting an example embodiment of a method 720 of using RF redirection device 300 with an on body device to accomplish data reception. Again, by way of example, specific references are made to the operation of device 300 within analyte monitoring system 100, although the use of device 300 is not limited to such. At 722, a second device (e.g., reader device 120, a relay device, a drug delivery device, etc.) transmits a first wireless RF signal to the on body device (e.g., sensor control device 102). This first RF signal can include, for example, a polling signal such as those used in the Bluetooth and BTLE protocols, a formatted request for data from the on body device, an activation command instructing the on body device 102 to power on or enter a relatively high-power state from a relatively low-power state, and the like.

At 724, the first RF signal can be received by the secondary antennas 302. At 726, the secondary antennas can output the received signal to the primary antenna 301. This can include transmission through RF power divider 303, which, in the reverse direction, acts additively to combine the power of each signal received by a secondary antenna 302 and output that sum total to the primary antenna 301. At 728, the primary antenna 301 propagates the sum total signal in the form of a second wireless RF signal. At 730, the second wireless RF signal can be received by the main antenna (e.g., antenna 261) of the on body device 102. At 732, the data in the received second wireless RF signal can be decoded and read by the on body device 102, and subsequently acted upon. In some embodiments, the first RF signal can be received by both the secondary antennas (step 724) and the main antenna 261, such that the on body device will receive at an even greater strength than with just main antenna 261.

Figure 8A:
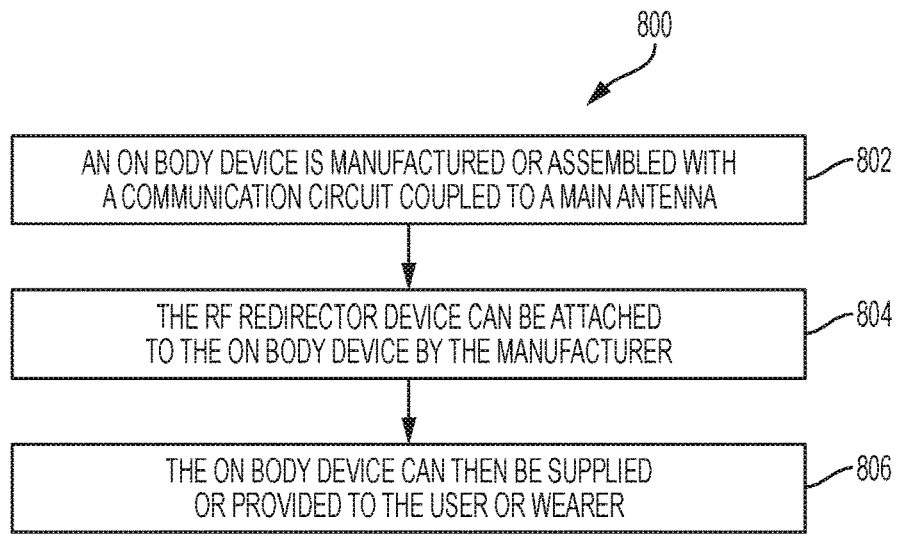
FIG. 8A is a flow diagram depicting an example embodiment of a method of assembling an on body device with an RF redirection device.

Also provided herein are example embodiments of methods of manufacturing, assembling, and/or applying an on body device. FIG. 8A is a flow diagram depicting an example embodiment of one such method 800. At 802, an on body device (e.g., sensor control device 102) is manufactured or assembled with a communication circuit (e.g., a transmitter, receiver, and/or transceiver) coupled to a main antenna (e.g., antenna 261). In some embodiments, the main antenna 261 is the only antenna of the manufactured or assembled on body device. At 804, RF redirector device 300 can be attached to the on body device 102 by the manufacturer. Device 300 can be configured as a flexible attachment like the example embodiments described with respect to FIGS. 4A-E. For example, device 300 can be adhesively applied to a housing of the on body device 102 and in some embodiments, this can occur prior to application of the on body device 102 to the wearer. Other forms of attachment can be used as well. At 806, the on body device 102 can then be supplied or provided to the user or wearer.

Figure 8B:
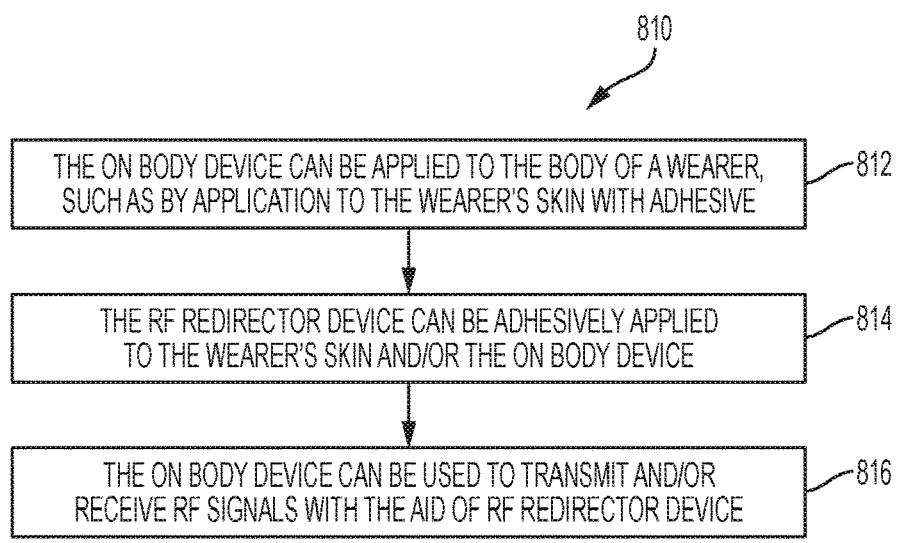
FIG. 8B is a flow diagram depicting an example embodiment of a method of applying an on body device.

FIG. 8B is a flow diagram depicting another example embodiment of a method 810 of applying an on body device (e.g., sensor control device 102) having a main antenna (e.g., antenna 261). In some embodiments, the main antenna 261 is the only antenna of the manufactured or assembled on body device. At 812, the on body device (e.g., sensor control device 102) can be applied to the body of a wearer, such as by application to the wearer's skin with adhesive (e.g., layer 105). At 814, device 300 can be adhesively applied to the wearer's skin and/or the on body device 102. For example, device 300 can be configured as a flexible attachment like the example embodiments described with respect to FIGS. 4A-E. The flexible attachment 300 can be applied only to the on body device 102 and not the wearer's skin, the flexible attachment 300 can be applied to both the wearer's skin and the on body device 102 (see FIG. 4B), or the flexible attachment can be applied to the wearer's skin adjacent the on body device 102 provided the primary antenna 301 is in the transmission path and near to the on body device's main antenna 261 (or one of the main antennas 261 if more than one). At 816, the on body device 102 can be used to transmit and/or receive RF signals with the aid of RF redirector device 300.

Figure 8C:
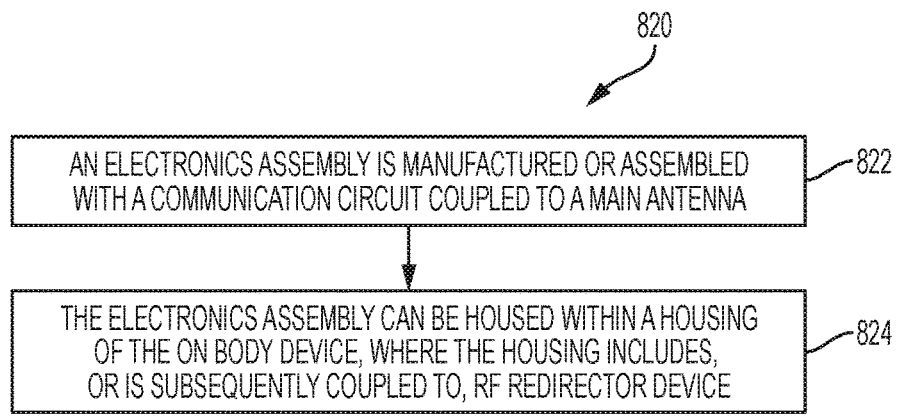
FIG. 8C is a flow diagram depicting another example embodiment of a method of assembling an on body device.

FIG. 8C is a flow diagram depicting an example embodiment of a method 820 of manufacturing or assembling an on body device (e.g., sensor control device 102). At 822, an electronics assembly (e.g., sensor electronics 250) is manufactured or assembled with a communication circuit coupled to a main antenna (e.g., antenna 261). In some embodiments, the main antenna 261 is the only antenna of the manufactured or assembled on body device 102. For example, the main antenna 261 can be the only antenna electrically connected to a sensor of the on body device 102 by way of conductive lines or traces present between the sensor and the main antenna 261 (such that there is no wireless communication between the sensor and the main antenna). At 824, the electronics assembly can be housed within a housing of the on body device 102, where the housing includes, or is subsequently coupled to, RF redirector device 300. For example, device 300 can be integrated with the housing in a manner like the example embodiments described with respect to FIGS. 5A-6B. At 826, the on body device can then be supplied or provided to the wearer.

An on body device coupled with an RF redirector device 300, similar to that described with respect to FIGS. 4A-E, was experimentally tested by performing transmissions on various channels using a BLTE protocol and compared with the on body device without the RF redirector device 300. Referencing the coordinate system of FIG. 4E, with a receiving antenna orientation in the X-Z plane, these tests showed improvements in the signal strength propagating from the on body device using the RF redirector device 300 in lateral X directions (i.e., the +X and −X directions) and in the upward longitudinal direction (i.e., the +Z direction) as compared to the version of the on body device without the RF redirector device 300.

Example Embodiments of Antenna Relocation Devices

In many example embodiments, the on body device can use a magnetic coupling technology to communicate an RF signal with the second device. One example of such a magnetic coupling technology is the NFC protocol known to those of ordinary skill in the art and also briefly described herein. Magnetic coupling technologies typically have a very short range, in many cases less than 12 inches, and even less than 3 inches. Because of this short range, magnetic coupling technologies are sometimes referred to as close proximity communications, and require the two communicating devices to be brought within range of each other. Devices communicating with magnetic coupling technologies typically use a loop antenna.

To communicate data between the devices, the user places the second device (e.g., reader device 120) directly over the on body device (e.g., sensor control device 102), within communication range and often in direct contact. For ease of reference, the process of communicating data between the second device and the on body device using a magnetic coupling technology will be referred to herein as "scanning."

In certain applications, such as in analyte monitoring environments, the on body device is positioned on the body in a location that is not always convenient to access for scanning. For example, sensor control device 102 may be placed on the back of the upper arm (e.g., adjacent the tricep), on the lower back, or on the upper abdomen, where device 102 may be difficult to reach with reader device 120 and/or obscured by clothing.

Example embodiments of secondary communication systems are disclosed that incorporate a second scannable antenna positioned in a more convenient location than the actual location of the on body device allowing the user to scan that second antenna instead of the on body device. For ease of reference, these example embodiments will be described in the context of an analyte monitoring environment with reference to sensor control device 102 as an example of the on body device and referenced to reader device 120 as an example of the second device.

Figure 9A:
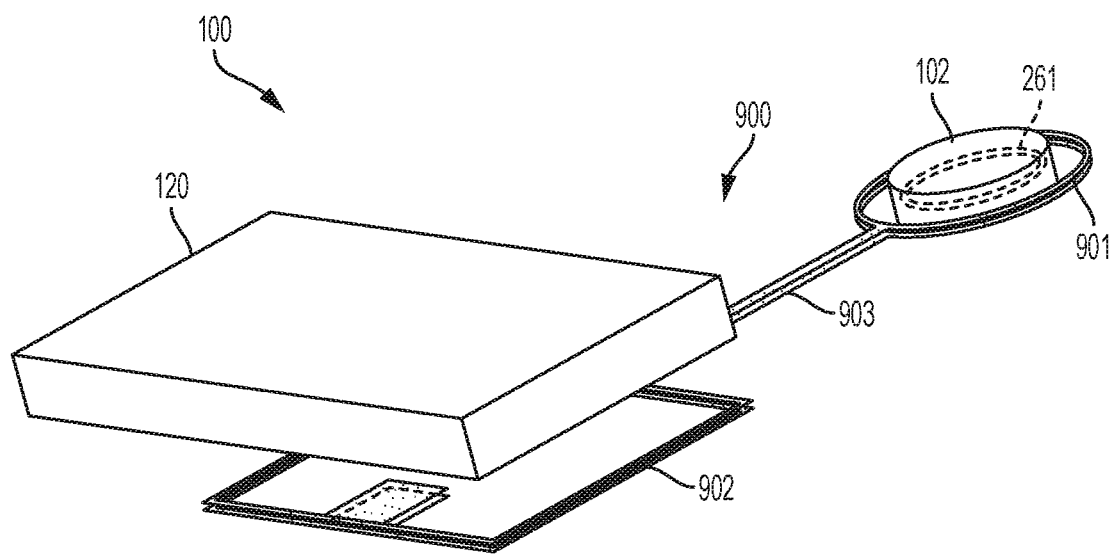
FIG. 9A is a perspective view depicting an example embodiment of an analyte monitoring system.

FIG. 9A is a perspective view depicting an example embodiment of system 100 configured to relocate the scanned location using an antenna relocation device 900. Here, antenna relocation device 900 includes a first primary antenna 901 coupled with a secondary antenna 902 by way of a conductive interconnect 903. Sensor control device 102 is shown with primary antenna 901 located about its periphery, within communication range of main antenna 261. Secondary antenna 902 is spaced away from primary antenna 901 by a predetermined distance (e.g., one inch, 6 inches, 12 inches, or more) with interconnect 903 spanning therebetween. Reader device 120 is shown in close proximity with secondary antenna 902 during the performance of a scan. Using a magnetic coupling technology, such as NFC, reader device 120 transmits a communication (e.g., a request for data) which is received by secondary antenna 902 and propagated along interconnect 903 to primary antenna 901, which in turn transmits the communication to a main antenna 261 (not shown) within the housing of on body device 102. Main antenna 261 can be part of a passive NFC communication circuit that does not require a separate power source for operation. Thus, antenna relocation device 900 can be a purely passive device, although in other embodiments device 900 can be an active device and utilize a power source to assist in transmission or reception.

Figure 9B:
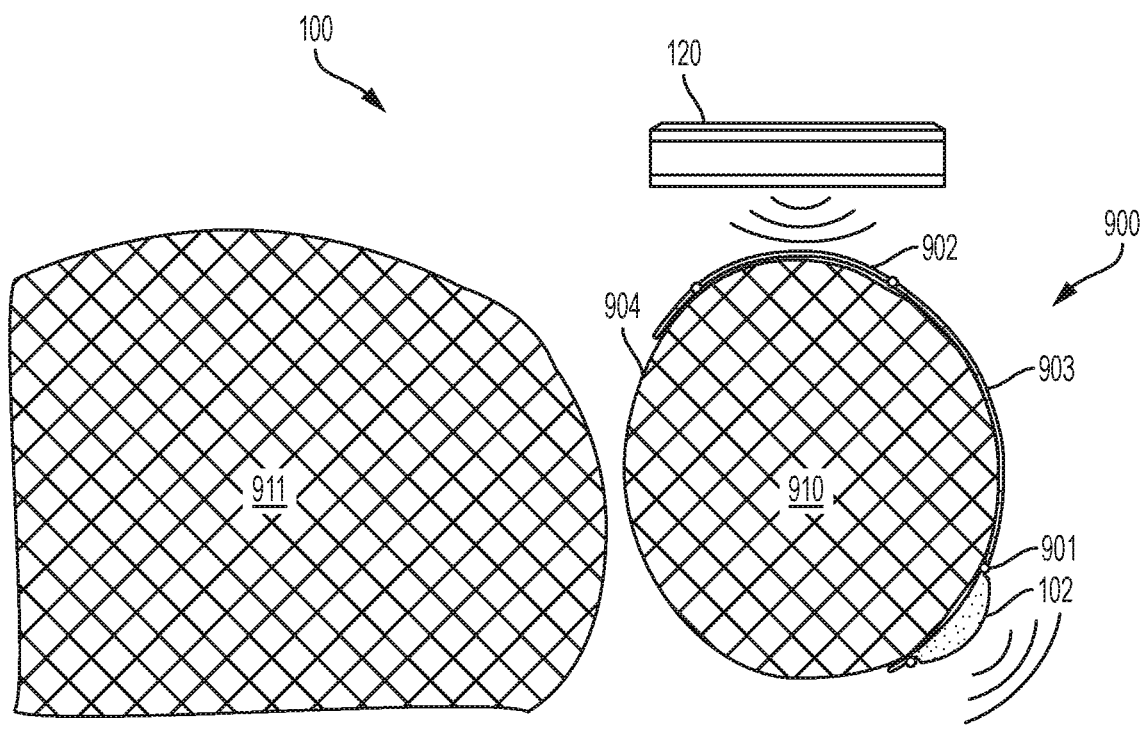
FIG. 9B is a cross-sectional view depicting another example embodiment of an analyte monitoring system during a scanning procedure by a user.

FIG. 9B is a cross-sectional view depicting system 100 during a scanning procedure with sensor control device 102 positioned posteriorly on a user's upper arm 910 adjacent the user's torso 911. Here, device 900 is coupled with a device holder 904 (e.g., an armband) that extends about the periphery of the user's upper arm 910. A user can scan secondary antenna 902 with reader device 120 on the anterior side of the user's arm, such as with the user's opposite arm, with greater ease than if the user were scanning the sensor control device 102 itself located on the generally opposite posterior side of arm 910.

Figure 9C:
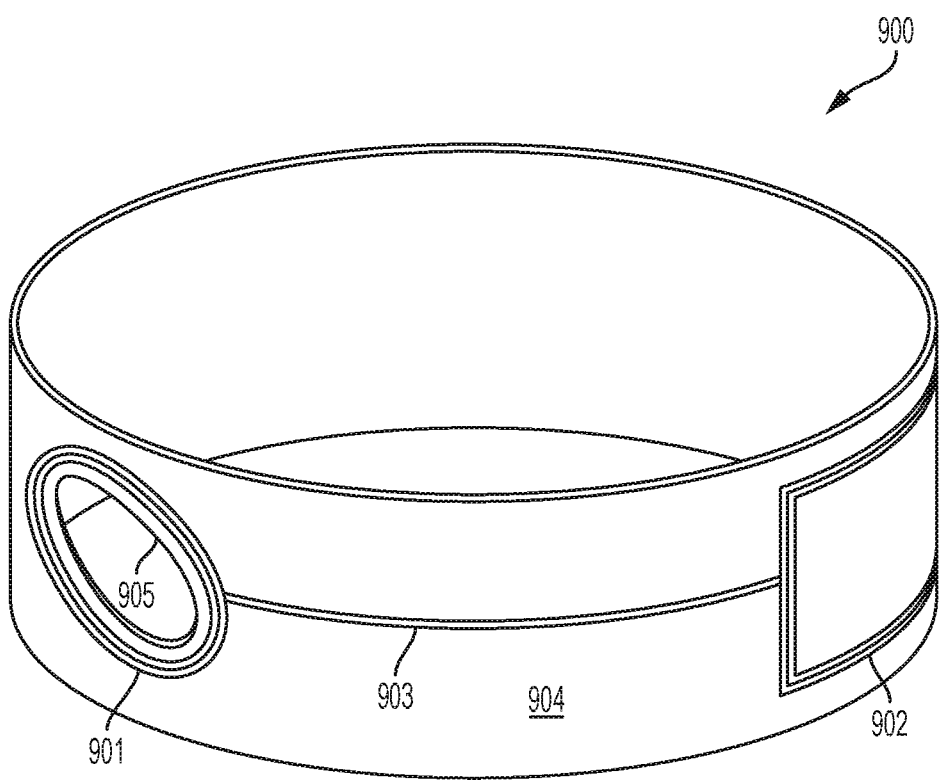
FIG. 9C is a perspective view depicting an example embodiment of an antenna relocation device coupled with a device holder.

FIG. 9C is a perspective view of an example embodiment of device 900 coupled with device holder 904. Band 904 includes an aperture 905 through which sensor control device 102 can extend. Primary antenna 901 can be positioned around aperture 905 such that placement over sensor control device 102 (not shown) automatically aligns primary antenna 901 with the internal antenna of sensor control device 102. Device holder 904 can be configured as a sleeve, band, strap, or otherwise. Device holder 904 can be composed of elastic materials such that holder can stretch and, in some embodiments, be applied to the body as an elastic band. Device holder 904 can also or alternatively be composed of inelastic materials. In some embodiments, device holder 904 includes a self-fastening device such as a snap, clip, buckle, hook and loop fastener such as a VELCRO fastener, or any combination thereof. Sensor control device 102 will typically be positioned on the user's arm first and then device holder 904 positioned over or around it. When device 900 is configured as a passive device, secondary antenna 902 can be used for scanning immediately after holder 904 is applied to the body and positioned with respect to sensor control device 102.

Figure 10A:
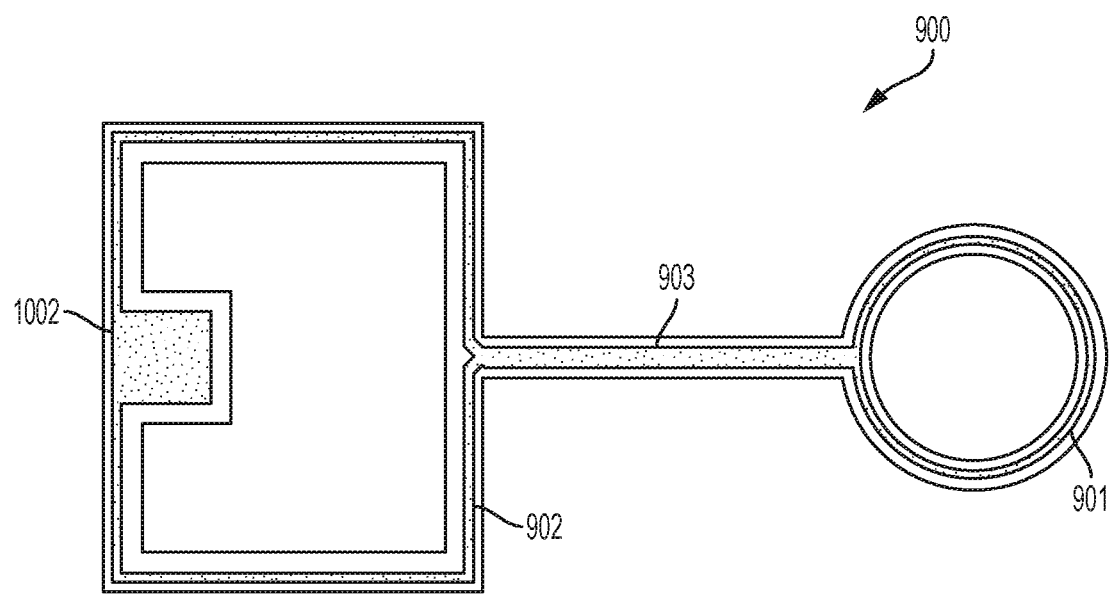
FIG. 10A is a top-down view of another example embodiment of an antenna relocation device.

FIG. 10A is a top-down view of device 900 where both primary antenna 901 and secondary antenna 902 are configured as loop antennas. In all of the embodiments described herein, the loop antennas can be shaped in an ellipsoidal or circular fashion, as with primary antenna 901 and main antenna 261 (not shown) or a polygonal fashion such as the rectangular configuration of secondary antenna 902, or in any other desired shape. In the embodiment of FIG. 10A, primary antenna 901 has a generally circular shape to match the profile of main antenna 261 (not shown) within sensor control device 102, while secondary antenna 902 has a generally rectangular shape to match the profile of those antennas commonly used in smart phones. In all embodiments of loop antennas described herein, each loop antenna can have a diameter, wire width, and number of turns (e.g., 1, 2, 3, 4, 5, 6, etc.) as desired for the specific application. Generally, more turns equate to more current induced by the magnetic field. Also, primary antenna 901 and secondary antenna 902 can have different shapes and different sizes as shown here, or they can have the same size and shape. In the embodiment depicted in FIG. 10A, a single conductive wire is used to form two loops for primary antenna 901 and two loops for secondary antenna 902 and the wire is twisted to form interconnect 903. A parasitic capacitor 1002 is electrically connected to device 900. In this embodiment, capacitor 1002 is formed by two conductive plates in parallel and is located in the interior of secondary antenna 902.

Figure 10B:
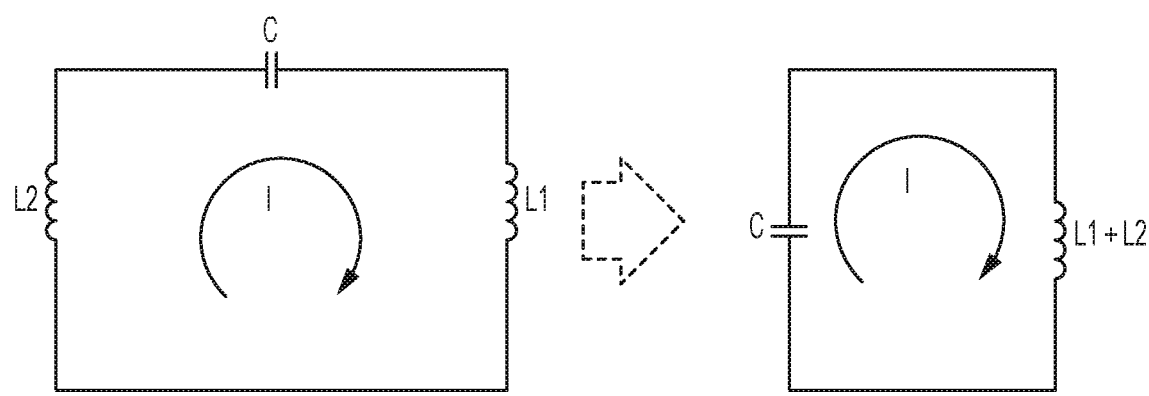
FIG. 10B is a circuit schematic depicting equivalent electrical circuits of the example embodiment described with respect to FIG. 10A.

FIG. 10B is a circuit schematic depicting equivalent electrical circuits of the example embodiment described with respect to FIG. 10A. In the circuit at left, inductor L1 represents the inductance of primary antenna 901 and inductor L2 represents the inductance of secondary antenna 902. The capacitance of capacitor 1002 is represented by C. The circuit at right represents an equivalent circuit of the one at left. The capacitance C and inductances L1 and L2 can be tuned according to formula (1) to achieve resonance at the desired carrier frequency F.

$$F = \frac{1}{2\pi\sqrt{(L1+L2)C}} \quad (1)$$

Figure 10C:
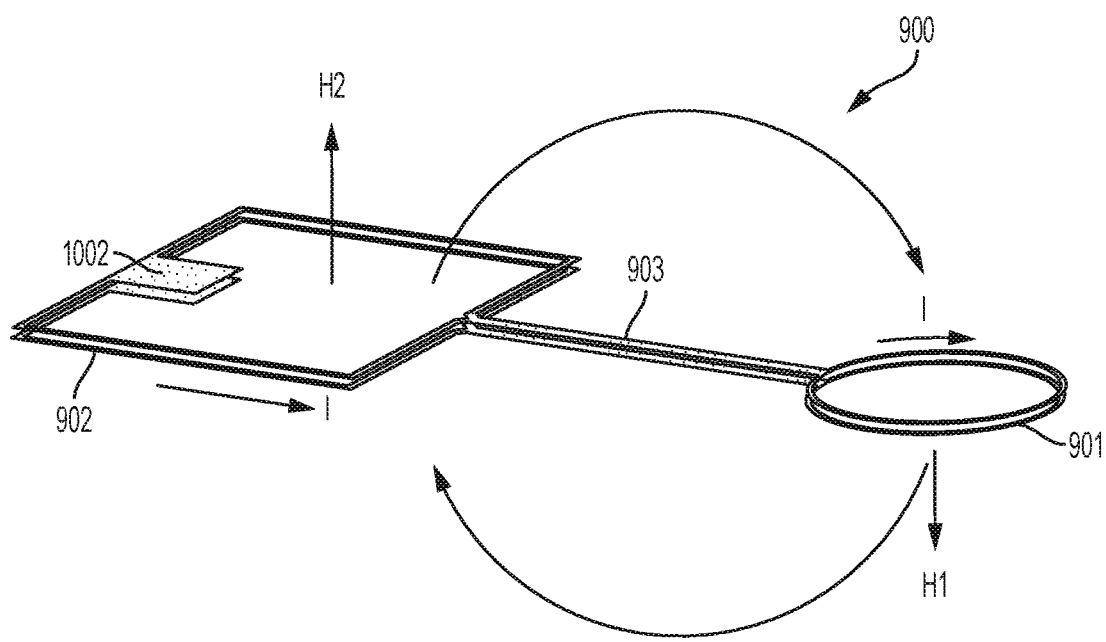
FIG. 10C as a perspective illustration depicting current directions and magnetic field lines with respect to an example embodiment of an antenna relocation device.

FIG. 10C as a perspective illustration depicting current directions and magnetic field lines that can be induced in device 900. The wire forming device 900 is twisted one or more times such that a current induced in secondary antenna 902 flows in a direction opposite to that in primary antenna 901. As shown here, the current I in secondary antenna 902 flows counterclockwise while the current I in primary antenna 901 flows clockwise. Current flow in this direction in secondary antenna 902 will generate a magnetic field indicated by the field direction H2, while current flow in the opposite direction in primary antenna 901 will generate a magnetic field indicated by the field direction H1, which is opposite or inverse to H2. In this configuration, the magnetic fields of H1 and H2 will circulate continuously as shown and not interfere with each other.

Figure 10D:
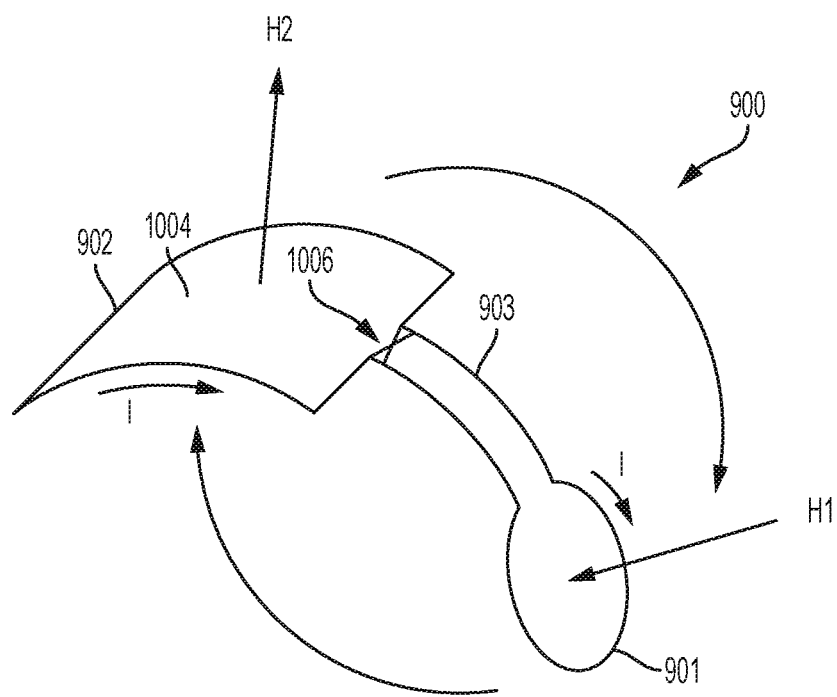
FIG. 10D is a perspective illustration depicting another example embodiment of an antenna relocation device.

FIG. 10D is a perspective illustration depicting another example embodiment of device 900. Here, primary antenna 901, secondary antenna 902, and interconnect 903 are formed by a conductive trace printed in a flexible substrate, such as a flexible printed circuit board (PCB). As shown here, the conductive trace crosses over itself at location 1006 such that the direction of current flow I in primary antenna 901 is again opposite to that in secondary antenna 902. Again, magnetic fields H1 and H2 are opposite and form a continuous field, such that the magnetic fields of H1 and H2 will not interfere with each other.

In one example embodiment of reception by sensor control device 102, reader device 120 generates a magnetic field H2 containing a transmission that when held in close proximity to secondary antenna 902 induces current flow I in a first direction around secondary antenna 902. This current I flows through primary antenna 901 in a second direction opposite to the first direction and generates the corresponding magnetic field H1 containing the transmission from reader 120. That magnetic field H1 generated by primary antenna 901 is received by main antenna 261 of sensor control device 102 and the transmission is thereby communicated from reader device 122 sensor control device 102.

Conversely, in an example embodiment of transmission by sensor control device 102, a response is generated by sensor control device 102 and transmitted by a magnetic field H1 propagated from main antenna 261 (e.g., a passive return transmission or backscatter transmission). Primary antenna 901 senses this magnetic field H1 and a current I is induced in a first direction around primary antenna 901. This current I also flows through secondary antenna 902 in a second direction opposite to the first direction and a corresponding magnetic field H2 is generated by secondary antenna 902, which is then sensed by the antenna of reader device 120. In this manner, the response transmission is communicated from sensor control device 102 to reader device 120.

Figure 11A:
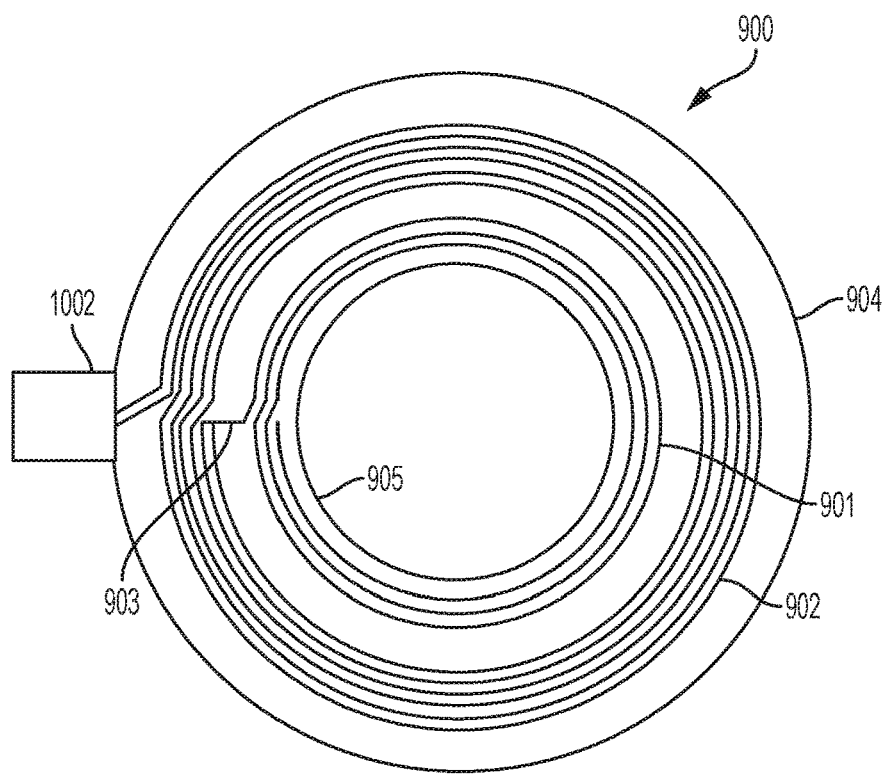
FIGS. 11A-B our top down views depicting another example embodiment of an antenna relocation device.

FIG. 11A is a top down view depicting another example embodiment of RF relocation device 900 where primary antenna 901 and secondary antenna 902 are aligned and share a common central axis. Here, device holder 904 includes an inner aperture 905. Outside of aperture 905 is primary antenna 901, which is in the form of a generally circular multi-loop antenna located about the periphery of inner aperture 905. Primary antenna 901 is connected to secondary antenna 902 by way of interconnect 903. Secondary antenna 902 is also in the form of a generally circular multi-loop antenna and is located around the outer periphery of primary antenna 901, resulting in a concentric arrangement of the two antennas 901 and 902. Secondary antenna 902 has two ends, one of which is connected to interconnect 903, and the other is connected to capacitive element 1002, which in this embodiment is in the form of a parallel plate capacitor that extends from an outer periphery of device holder 904 like a polygonal tab. Although not shown, capacitor 1002 is also connected to an end of primary antenna 901 in order to close the antenna circuit.

Figure 11B:
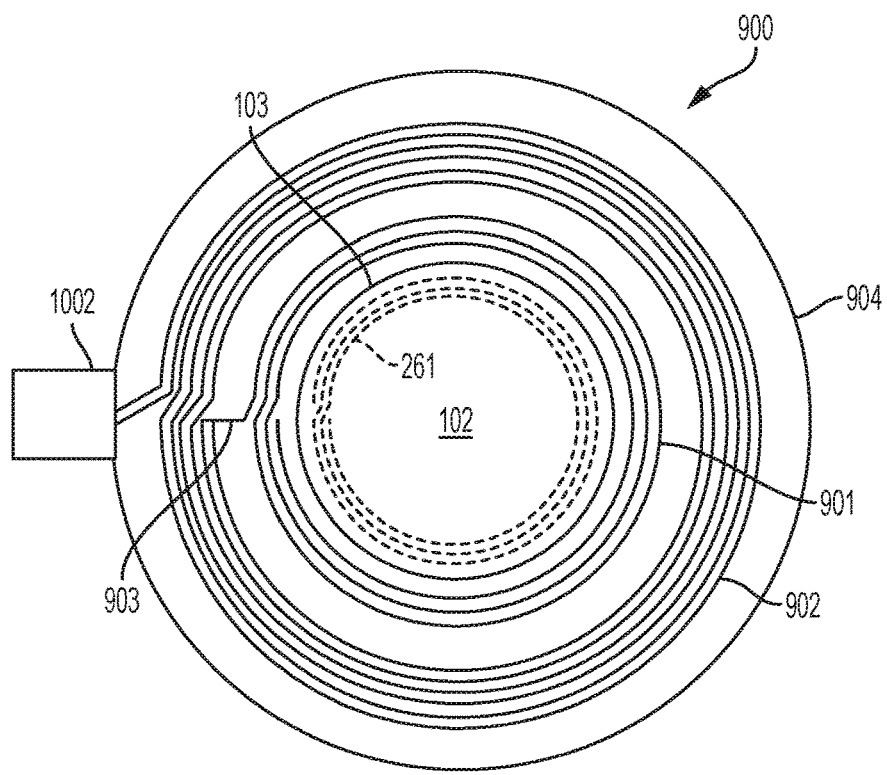

FIG. 11B is a top down view depicting this embodiment of RF relocation device 900 but with sensor control device 102 located within inner aperture 905 (not shown). The interior electrical components of sensor control device 102 are not shown with the exception of main antenna 261, which is indicated via dashed lines to indicate its presence within housing 103. As shown here, main antenna 261 is also configured as a generally circular multi-loop antenna that is adjacent the outer periphery of housing 103 and the inner periphery of device holder 904. Main antenna 261 is also concentric to primary antenna 901 and secondary antenna 902. Stated differently, all three antennas are aligned and share a common center axis (normal to the page). Because the antennas are aligned the magnetic fields will also tend to align and thus, in this embodiment, interconnect 903 does not include a twist and current is permitted to flow in the same direction in all three antennas (e.g., the current flows clockwise in all three antennas or counterclockwise in all three antennas) so that the magnetic fields do no counteract each other. However, device 900 can be configured such that current runs in opposite directions if desired.

The operation of this embodiment of device 900 is similar to those described with respect to the embodiments of FIGS. 9A-10D in that an RF signal transmitted by a second device is received by secondary antenna 902 and communicated to primary antenna 901 which subsequently retransmits the RF signal to main antenna 261. Because secondary antenna 902 has a diameter or width that is larger than the diameters of main antenna 261 and primary antenna 901, the overall device is provided with an overall larger antenna. This can make a scanning process easier for the user, since the user need only establish a magnetic coupling between the antenna of the second device (e.g., reader device 120) and the much larger secondary antenna 902. For example, the user may establish communication with device 102 by placing the second device in a position that does not align the second device's antenna with main antenna 261 but is rather significantly laterally offset from antenna 261, so long as within range of the larger secondary antenna 902. Use of device 900 can therefore effectively provide a larger target for scanning on body device 102.

While antennas 261, 901, and 902 are shown to be generally circular in this embodiment, these antennas can be implemented in any of the other shapes (e.g., polygonal, ellipsoidal, etc.). Also, in FIGS. 11A-B secondary antenna 902 is shown to have a larger conductive trace width than primary antenna 901. In other embodiments, these widths can be the same. These widths can also be the same as, or different from, that of main antenna 261. Furthermore, as with the other embodiments described herein, the number of loops in each antenna 261, 901, and 902 can vary (e.g., one or more) and each antenna can have the same or a different number of loops as compared to the other antennas of the device.

While device holder 904 has an inner aperture 905 in this embodiment to permit placement of device 102, this aperture 905 need not be present and device holder 904 can be positioned beneath sensor control device 102 or over top of sensor control device 102 (e.g., in a manner like that shown in FIG. 4B for device 300). In some embodiments, device holder 904 can itself be the underlying adhesive pad 105 of sensor control device 102, and in other embodiments device holder 904 can be connected directly to adhesive pad 105 on the user's skin.

Figure 12A:
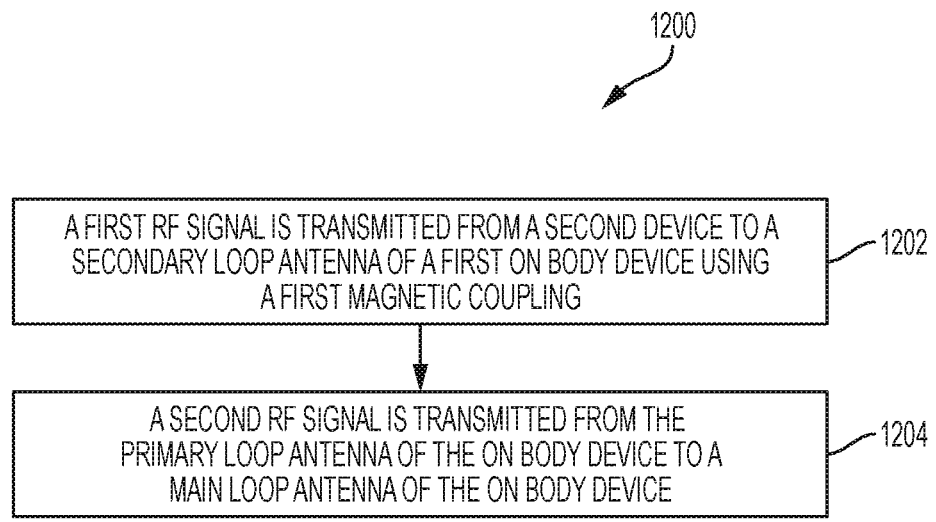
FIG. 12A is a flow diagram depicting an example embodiment of a method of receiving data by an on body device with a relocation device.

FIG. 12A is a flow diagram depicting an example embodiment of a method 1200 of receiving data by the on body device using RF relocation device 900. At 1202, a first RF signal is transmitted from a second device (e.g., reader device 120) to a secondary loop antenna 902 of a first on body device (e.g., sensor control device 102) using a first magnetic coupling. In some embodiments, transmission of the first RF signal occurs by application of a first magnetic field to the secondary loop antenna 902 and induces a current in a first direction around the secondary loop antenna 902, and the current flows in a second direction around the primary loop antenna 901. At 1204, a second RF signal is transmitted from the primary loop antenna 901 of the on body device to a main loop antenna (e.g., antenna 261) of the on body device. The first RF signal comprises data which is similarly conveyed by the second RF signal. Although not shown here, in some embodiments the primary loop antenna and the secondary loop antenna are coupled to a band, and the method 1200 can include applying the band to the body of a user such that the primary loop antenna is within communication range of the main loop antenna.

Figure 12B:
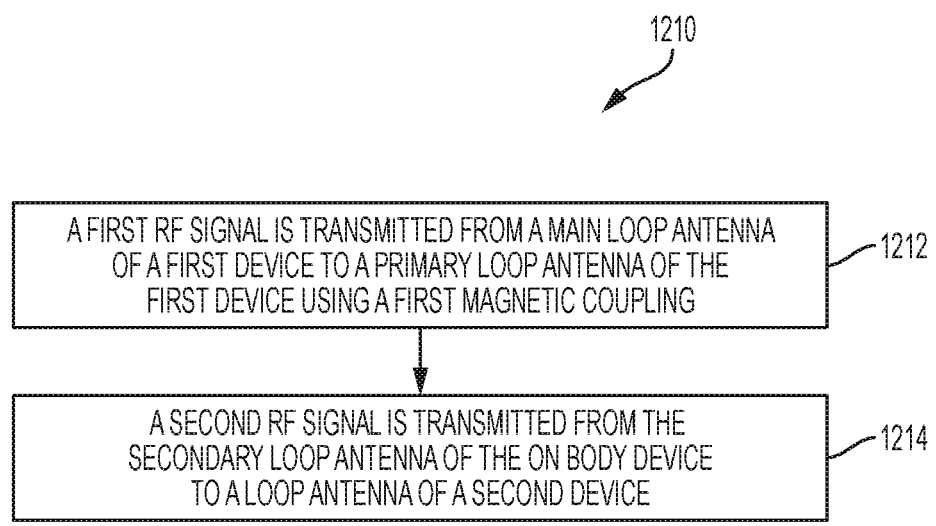
FIG. 12B is a flow diagram depicting an example embodiment of a method of transmitting data by an on body device using a relocation device.

FIG. 12B is a flow diagram depicting an example embodiment of a method 1110 of transmitting data by the on body device using relocation device 900. At 1212, a first RF signal is transmitted from a main loop antenna of a first device (e.g., sensor control device 102) to primary loop antenna 901 of the first device using a first magnetic coupling. In some embodiments, transmission of the first RF signal occurs by application of a first magnetic field to the primary loop antenna and induces a current in a first direction around the primary loop antenna, and the current flows in a second direction around the secondary loop antenna 902. At 1214, a second RF signal is transmitted from the secondary loop antenna 902 of the on body device to a loop antenna of a second device (e.g., reader 120). The first RF signal comprises data which is similarly conveyed by the second RF signal. Although not shown here, in some embodiments the primary loop antenna and the secondary loop antenna are coupled to a band, and the method 1210 can include applying the band to the body of a user such that the primary loop antenna is within communication range of the main loop antenna.

The transmissions communicated from the on body devices and from the second devices disclosed herein can contain any desired type of data or information. With respect analyte monitoring, all types of communications described herein (e.g., pulling signals, requests for data, raw analyte data, processed analyte data, temperature data, and others) can be communicated between the on body device and the second device using any and all of the embodiments described with respect to FIGS. 3-11B.

For each and every embodiment of a method disclosed herein, systems and devices capable of performing each of those embodiments are covered within the scope of the present disclosure. For example, embodiments of sensor control devices are disclosed, and these devices can have one or more sensors, analyte monitoring circuits (e.g., an analog circuit), memories (e.g., for storing instructions), power sources, communication circuits, transmitters, receivers, processors and/or controllers (e.g., for executing instructions) that can perform any and all method steps or facilitate the execution of any and all method steps. These sensor control device embodiments can be used and can be capable of use to implement those steps performed by a sensor control device from any and all of the methods described herein.

Computer program instructions for carrying out operations in accordance with the described subject matter may be written in any combination of one or more programming languages, including an object-oriented programming language such as Java, JavaScript, Smalltalk, C++, C#, Transact-SQL, XML, PHP or the like and conventional procedural programming languages, such as the "C" programming language or similar programming languages. The program instructions may execute entirely on the user's computing device, partly on the user's computing device, as a standalone software package, partly on the user's computing device and partly on a remote computing device or entirely on the remote computing device or server. In the latter scenario, the remote computing device may be connected to the user's computing device through any type of network, including a local area network (LAN) or a wide area network (WAN), or the connection may be made to an external computer (for example, through the Internet using an Internet Service Provider).

It should be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

To the extent the embodiments disclosed herein include or operate in association with memory, storage, and/or computer readable media, then that memory, storage, and/or computer readable media are non-transitory. Accordingly, to the extent that memory, storage, and/or computer readable media are covered by one or more claims, then that memory, storage, and/or computer readable media is only non-transitory.

In many instances, entities are described herein as being coupled to other entities. It should be understood that the terms "coupled" and "connected" (or any of their forms) are used interchangeably herein and, in both cases, are generic to the direct coupling of two entities (without any non-negligible intervening entities) and the indirect coupling of two entities (with one or more non-negligible intervening entities). Where entities are shown as being directly coupled together, or described as coupled together without description of any intervening entity, it should be understood that those entities can be indirectly coupled together as well unless the context clearly dictates otherwise.

As used herein and in the appended claims, the singular forms "a," "an," and "the" include plural referents unless the context clearly dictates otherwise.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

What is claimed is:

1. An electronic device, comprising:
   an on body device comprising a communication circuit coupled with a main loop antenna;
   a primary loop antenna; and
   a secondary loop antenna connected to the primary loop antenna by an interconnect,
   wherein the secondary loop antenna is adapted to receive a first radio frequency (RF) and induce the transmission of a second RF signal by the primary loop antenna to the main antenna.

2. The device of claim 1, wherein the primary loop antenna is positioned about the perimeter of the on body device.

3. The device of claim 1, wherein the device is configured such that a magnetic field applied to the secondary loop antenna induces a current in a first direction around the secondary loop antenna and the current flows in a second direction around the primary loop antenna.

4. The device of claim 3, wherein the first direction is opposite to the second direction.

5. The device of claim 3, wherein the first direction is counterclockwise in the second direction is clockwise.

6. The device of claim 3, wherein the interconnect is twisted.

7. The device of claim 1, wherein a single conductive wire or trace forms the primary loop antenna, the secondary loop antenna, and the interconnect.

8. The device of claim 1, wherein the main loop antenna, the primary loop antenna, and the secondary loop antenna are aligned and share a common central axis.

9. The device of claim 8, wherein the primary loop antenna and the secondary loop antenna are coupled with a device holder having an aperture in which the on body device is located.

10. The device of claim 1, wherein the main loop antenna, the primary loop antenna, and the secondary loop antenna are adapted to operate according to a Near Field Communication (NFC) protocol.

11. A method of radio frequency transmission, comprising:
    transmitting a first radio frequency (RF) signal from a second device to a secondary loop antenna of a first device using a first magnetic coupling, wherein the secondary loop antenna is electrically connected to a primary loop antenna of the first device; and
    transmitting a second RF signal from the primary loop antenna to a main loop antenna of the first device using a second magnetic coupling, wherein the first RF signal comprises data and the second RF signal is generated from the first RF signal and comprises the data.

12. The method of claim 11, wherein the first device is an on body device comprising a sensor.

13. The method of claim 12, wherein the primary loop antenna and the secondary loop antenna are coupled to an adhesive pad of the on body device.

14. The method of claim 11, wherein transmission of the first RF signal occurs by application of a first magnetic field to the secondary loop antenna and induces a current in a first direction around the secondary loop antenna.

15. The method of claim 14, wherein the current flows in a second direction around the primary loop antenna.

16. The method of claim 15, wherein the first direction is opposite to the second direction.

17. The method of claim 11, wherein the main loop antenna, the primary loop antenna, and the secondary loop antenna are aligned and share a common central axis.

18. The method of claim 17, wherein the primary loop antenna and the secondary loop antenna are coupled with a device holder having an aperture in which the on body device is located.

19. The method of claim 11, wherein the main loop antenna, the primary loop antenna, and the secondary loop antenna are adapted to operate according to a Near Field Communication (NFC) protocol.

20. The device of claim 1, further comprising a device holder coupled to the primary loop antenna and the secondary loop antenna, wherein the device holder is an adhesive pad of the on body device.

* * * * *